US011077413B2

(12) United States Patent
Djupevåg et al.

(10) Patent No.: US 11,077,413 B2
(45) Date of Patent: Aug. 3, 2021

(54) MIXING AND PROCESSING APPARATUS

(71) Applicant: ALKYMAR AS, Haugsvær (NO)

(72) Inventors: Olav Asle Djupevåg, Bønes (NO);
Arnstein Haugen, Lysekloster (NO);
Ole Jørgen Marvik, Jar (NO); Kjartan Sandnes, Haugsvær (NO)

(73) Assignee: ALKYMAR AS, Haugsvær (NO)

( * ) Notice: Subject to any disclaimer, the term of this patent is extended or adjusted under 35 U.S.C. 154(b) by 136 days.

(21) Appl. No.: 16/083,733

(22) PCT Filed: Mar. 17, 2017

(86) PCT No.: PCT/EP2017/056455
§ 371 (c)(1),
(2) Date: Sep. 10, 2018

(87) PCT Pub. No.: WO2017/158188
PCT Pub. Date: Sep. 21, 2017

(65) Prior Publication Data
US 2019/0381468 A1    Dec. 19, 2019

(30) Foreign Application Priority Data

Mar. 17, 2016 (GB) ..................................... 1604529

(51) Int. Cl.
*B01F 9/02*  (2006.01)
*B01F 9/00*  (2006.01)
(Continued)

(52) U.S. Cl.
CPC .......... *B01F 9/025* (2013.01); *B01F 7/00391* (2013.01); *B01F 9/001* (2013.01);
(Continued)

(58) Field of Classification Search
CPC ...... B01F 7/00391; B01F 9/001; B01F 9/025; B01F 9/06; B01F 9/16; C12M 21/18; C12M 27/10
See application file for complete search history.

(56) References Cited

U.S. PATENT DOCUMENTS 770,477 A    9/1904  Ransome
2,076,163 A  4/1937  Ryan et al.
(Continued)

FOREIGN PATENT DOCUMENTS

CN    102555060 A    7/2012
CN    103468563 A    12/2013
(Continued)

OTHER PUBLICATIONS

Search Report for United Kingdom Patent Application No. 1604529. 6, dated Aug. 18, 2016, 3 pages.
(Continued)

*Primary Examiner* — Tony G Soohoo
(74) *Attorney, Agent, or Firm* — Withrow & Terranova, P.L.L.C.; Vincent K. Gustafson

(57) ABSTRACT

A rotating drum apparatus for the mixing and processing of materials, the rotating drum apparatus comprising: a rotating drum (12) arranged with the length of the drum and the axis of rotation of the drum extending along the horizontal; an inlet at a first point on the drum (12) for receiving materials prior to mixing and/or processing; a screw (14) within the drum (12) for mixing the materials whilst conveying them lengthwise along the drum (12), wherein the screw (14) includes a helical blade extending along the length of the drum (12) with the outer edge of the helical blade being fixed to the inner surface of the drum (12) such that material can be conveyed and mixed in separated volumes (16) between each turn of the screw blade (14); an outlet at a second point along the drum for discharge of materials after (Continued)

mixing and/or processing; and a plurality mixing devices (18) for promoting mixing of the material in each of the separated volumes (16) of material as the material is conveyed along the screw (14), wherein the plurality of mixing devices (18) are spaced apart along the blade of the screw (14), and wherein there is at least one mixing device (18) for each turn of the screw blade (14).

22 Claims, 5 Drawing Sheets

(51) Int. Cl.
*B01F 9/06* (2006.01)
*C12M 1/40* (2006.01)
*C12M 3/04* (2006.01)
*B01F 7/00* (2006.01)
*B01F 9/16* (2006.01)

(52) U.S. Cl.
CPC .............. *B01F 9/06* (2013.01); *B01F 9/16* (2013.01); *C12M 21/18* (2013.01); *C12M 27/10* (2013.01)

(56) References Cited

U.S. PATENT DOCUMENTS

| | | | |
|---|---|---|---|
| 4,126,517 A | 11/1978 | Bayer | |
| 4,199,371 A | 4/1980 | Regnault et al. | |
| 4,974,781 A | 12/1990 | Placzek | |
| 5,119,994 A | 6/1992 | Placzek | |
| 5,683,177 A | 11/1997 | Hoferichter et al. | |
| 7,204,636 B2* | 4/2007 | Didion | B01F 9/06 |
| | | | 34/137 |
| 2002/0096269 A1 | 7/2002 | Bouchette et al. | |
| 2005/0051286 A1 | 3/2005 | Carels et al. | |
| 2005/0236320 A1* | 10/2005 | Didion | B01F 15/063 |
| | | | 210/323.1 |
| 2007/0190643 A1* | 8/2007 | Noll | C12M 23/50 |
| | | | 435/290.3 |
| 2009/0092752 A1 | 4/2009 | Brandt, Jr. et al. | |
| 2009/0215000 A1* | 8/2009 | Boots | B09B 3/00 |
| | | | 432/118 |
| 2011/0121112 A1 | 5/2011 | Alford | |

FOREIGN PATENT DOCUMENTS

| | | |
|---|---|---|
| EP | 0566877 B1 | 11/2002 |
| FR | 898980 A | 5/1945 |
| GB | 1152238 A | 5/1969 |
| GB | 1328724 A1 | 8/1973 |
| GB | 2477422 A | 8/2011 |
| JP | S58223429 A | 12/1983 |
| JP | S62114637 A | 5/1987 |
| RU | 1787416 A1 | 1/1993 |
| RU | 2490323 C1 | 8/2013 |
| SU | 1604450 A1 | 11/1990 |
| WO | 2004049818 A1 | 6/2004 |
| WO | 2006015423 A1 | 2/2006 |
| WO | 2012172329 A2 | 12/2012 |
| WO | 2016041896 A1 | 3/2016 |

OTHER PUBLICATIONS

International Search Report and Written Opinion for PCT/EP2017/056455, dated Oct. 9, 2017, 20 pages.

Helix Angle: Definition, Formula & Calculation. Study.com [retrieved on May 20, 2021.] Retrieved from the Internet: <URL:https://study.com/academy/lesson/helix-angle-definition-formula-calculation.html>.

First Office Action for Chinese Patent Application No. 201780023726.9, dated Dec. 30, 2020, 24 pages.

Examination Report for Indian Patent Application No. 201817037136, dated Feb. 9, 2021, 7 pages.

* cited by examiner

MIXING AND PROCESSING APPARATUS

This application is a 35 U.S.C. § 371 national phase filing of International Application No. PCT/GB2017/056455 filed on Mar. 17, 2017, and claims the benefit of United Kingdom Patent Application No 1604529.6 filed on Mar. 17, 2016, wherein the disclosures of the foregoing applications are hereby incorporated by reference herein in their respective entireties.

The present invention relates to an apparatus and method for mixing and processing materials, for example for enzymatic processing of organic material.

There is a need for mixing and processing of materials in various industries including situations where a simple mechanical mixing is necessary, for example to create slurries or other mixtures from raw materials including both solids and liquids, as well as for biological processing of materials to change the nature of the materials such as during fermentation and other microbial processing, hydrolysis and other enzymatic processing steps. The processing of materials might include the extraction of proteins from animal sources (for example from fish/shellfish) or from vegetable sources (for example from peas), with enzymes used to dissolve the raw materials in a processing area with mixing and/or turbulence. Purely chemical processes could be used in a similar fashion or for other modifications to the raw materials. Similar processing can also be carried out using micro-organisms and the like.

Enzymatic processing of organic molecules encompasses at least the following processes: oxidation/reduction (by oxidoreductases), transfer of a functional group, e.g. a methyl or phosphate group (by transferases), hydrolysis (by hydrolases), cleavage of various bonds by means other than hydrolysis and oxidation (by lyases), isomerization changes within a single molecule (by isomerases) and joining of two molecules with covalent bonds (by ligases). Organic molecules include macromolecules, for example proteins, lipids and polysaccharides as present in various types of biomass.

In enzymatic hydrolysis, chemical bonds in a molecule are broken by the addition of water, with an enzyme acting as a catalyst for the reaction. To promote this reaction, the various components of the reaction mixture (for example, the raw material comprising the molecules to be hydrolysed, water, and an appropriate enzyme) must be mixed together under appropriate reaction conditions. As an example, proteins obtained from marine biological sources (e.g. algae, crustaceans, or fish-derived material) can be processed by hydrolysis to obtain a wide array of peptides all the way down to single amino acids—depending on the enzymes used and the processing conditions.

Mixing the various components of the reaction mixture is necessary, regardless of whether the reaction taking place is hydrolysis or is another form of enzymatic or microbial processing. Thus, whilst hydrolysis is the focus of the following discussion, the technical considerations and the invention itself are equally applicable to enzymatic processing more generally.

WO-A-2004/049818 discloses a plant for hydrolysis of protein-containing raw material. The plant includes a hydrolysis area comprising a pipe in which is provided a rotating auger to convey and gently mix the reaction mixture. It is recognised that mixing must be carried out in a controlled manner to control contact between the enzymes and raw material, whilst avoiding (or minimizing the degree of) formation of an emulsion. The process can be run as a continuous process or as a batch process.

EP-B-0566877 discloses an apparatus for the enzymatic hydrolysis of proteins, in which hydrolysis is carried out in a tube provided with static mixing elements. The static mixing elements comprise metal or plastic braces nested into each other. However, this apparatus may not be able to perform the same hydrolysis reactions or provide the same operational advantages, level of efficiency or consistency as are described in WO-A-2004/049818, since it is not possible to have a continuous reaction process with the apparatus of EP-B-0566877.

Therefore, there is a need to provide an alternative technique for mixing materials such as reagents in an enzymatic or microbial processing plant, as well as other materials such as for pre-processing of biological matter, for example plant and animal materials used in the manufacture of food products.

According to a first aspect of the present invention, there is provided a rotating drum apparatus for the mixing and processing of materials, the rotating drum apparatus comprising: a rotating drum arranged with the length of the drum and the axis of rotation of the drum extending along the horizontal; an inlet at a first point on the drum for receiving materials prior to mixing and/or processing; a screw within the drum for mixing the materials whilst conveying them lengthwise along the drum, wherein the screw includes a helical blade extending along the length of the drum with the outer edge of the helical blade being fixed to the inner surface of the drum such that material can be conveyed and mixed in separated volumes between each turn of the screw blade; an outlet at a second point along the drum for discharge of materials after mixing and/or processing; and a plurality mixing devices for promoting mixing of the material in each of the separated volumes of material as the material is conveyed along the screw, wherein the plurality of mixing devices are spaced apart along the blade of the screw, and wherein there is at least one mixing device for each turn of the screw blade.

With the arrangement of this apparatus the material that is to be mixed and processed progresses from the inlet to the outlet along the turns of the screw whilst undergoing mixing due to the rotation of the drum, the "pushing" of the blade of the screw to convey the material lengthwise along the drum, and also due to the addition of mixing devices spaced apart along the blade of the screw. This can produce more effective mixing and processing of materials than prior art devices that do not include additional mixing devices at each turn of the screw. By placing the mixing devices spaced apart along the screw and having at least one mixing device for each turn of the screw then the mixing devices act on each volume of the material as it is conveyed along the screw.

The rotating drum apparatus may for example be for use in enzymatic processing, such as for hydrolysis of protein, triglycerides, cellulose or chitin and the like, as well as other types of processing as discussed above. The rotating drum apparatus may alternatively be for use in other mixing and processing applications, such as for mixing raw materials in the preparation of food products or fertilisers, for the manufacture of pulp or slurry products, for the separation of materials in waste processing and so on. If the drum is made air tight at the inlet and outlet, and optionally provided with a suitable vent for releasing excess pressure, then it would be suitable as a continuous bioreactor in anaerobic digestion of various types of biomass, including waste material such as manure and sludge from aquaculture. Depending on the speed of rotation, it could even be used in other types of biological cultivation, e.g. the cultivation of insect larva.

The helical screw blade forms a series of enclosed volumes between each turn of the blade. In order that the apparatus can be used with fluid raw materials the screw blade is preferably attached at its outer edge to the internal surface of the drum with a watertight join. With this arrangement the screw blade forms a sequence of enclosed chambers where separate batches of material can be processed without direct contact with adjacent batches of material. Advantageously, this allows for different reaction mixtures to be used in the different chambers, for example by introducing additional reactants as the material is conveyed along the length of the drum. As explained below, this can be done via the mixing devices in some examples, as in the preferred embodiment.

It is preferred for there to be multiple mixing devices for each turn of the screw, for example there may be a sufficient number of mixing devices so that at least one of the mixing devices is always in contact with the material as it is conveyed along the screw. It will be appreciated that in this type of rotating screw device the material that is being mixed and conveyed sits in the base of the device in the chambers that are formed between the turns of the screw and there is a headspace above the level of the material. In order to obtain best effect from the mixing devices it is advantageous for there to always be a mixing device below the level of the material and contacting the material so that there is never any period when the material is not subject to the action of the mixing device. For example, if the level of the material within the drum during normal use can be approximated as a segment of a circle (assuming a cylindrical drum) formed by a chord subtending an arc of 90° then if there are four equally spaced mixing devices on each 360 degree turn of the blade of the screw then there will always be a mixing device in contact with the material. There may be four or more mixing devices for each turn of the blade of the screw, optionally five or more, or six or more. A greater number of mixing devices could be included either when the level of material within the drum is expected to be low enough to require a smaller spacing between the devices during normal use, or when it is considered to be an advantage to have more than one mixing device in contact with the material at any one time.

The mixing devices may comprise mixing vanes spaced apart along the screw with multiple vanes for each turn of the screw, the vanes being arranged to promote mixing of the material to be processed. Each of the plurality of mixing devices may comprise a mixing vane, or alternatively there may be multiple types of mixing devices of which only some of the plurality of mixing devices comprise a mixing vane. A mixing vane preferably takes the form of an element mounted to the blade of the screw with a surface having a greater angle of attack than the surface of the blade of the screw. Thus, the mixing vane may include a ramp surface with a greater angle of attack than the surface of the screw blade. Each mixing vane may include an identical ramp surface with the same angle of attack, or alternatively the angle of ramp surface for the mixing vane may vary, for example with an increase in the angle of attack or a decrease in the angle of attack for the mixing vane depending on its position along the extent of the blade of the screw. In one example the ramp surface of the mixing vane is an upper surface of a wedge shaped element with the lower surface of the wedge shaped element being adjacent the surface of the blade of the screw and either attached thereto or integrally formed therewith, for example it may be attached by welding or formed with the blade of the screw in a casting process. The mixing vane may be considered to have a leading-edge at the start of the ramp surface, where in use the mixing vane first enters the material held within the volume between two turns of the screw, and a trailing edge at the end of the ramp surface which is furthest from the surface of the screw blade, the trailing edge being the edge that last meets the material held within the screw. In the case where a wedge shaped element is used then the trailing edge would be the apex of the wedge shaped element at the point furthest from the surface of the screw blade. That is, the leading edge is the end of the ramp surface at the thin end of the wedge, and the trailing edge is the end of the ramp surface at the thick end of the wedge.

A trailing end surface of the wedge shaped element extending from the trailing edge to the screw blade may meet the surface of the screw blade at an angle close to perpendicular, for example an angle within 20 degrees of perpendicular or an angle within 10 degrees of perpendicular. The trailing end surface may meet the screw blade surface at an angle of about 90 degrees. Alternatively, the trailing end surface of the wedge shaped element may meet the surface of the screw blade at an angle of greater than 90 degrees or less than 90 degrees. The trailing end surface of the wedge shaped element may also meet the inner wall of the drum, i.e. the wedge may be at the outer edge of the screw blade adjacent the drum inner wall. In this case the trailing end surface may meet the inner wall of the drum at an angle close to perpendicular, for example an angle within 20 degrees of perpendicular or an angle within 10 degrees of perpendicular. The trailing end surface may meet the drum inner wall at an angle of about 90 degrees.

It is advantageous for the mixing vane to be mounted at the outer part of the surface of the screw blade, i.e. adjacent to the inner wall of the drum. This means that the mixing vane will affect mixing of all of the materials in the volume between two turns of the screw, including at the deepest extent of those materials. The mixing vane may extend from the inner wall of the drum along the surface of the screw blade toward the centre of rotation of the drum. The mixing vane could extend toward the centre of rotation to the same extent as the screw blade or to a lesser extent. The screw blade would typically extend sufficiently far toward the centre of the drum so as to be above the level of the material held in each volume between turns of the screw. This avoids any intermixing of materials from adjacent turns. The mixing vane may extend toward the centre of the drum to a lesser extent than the screw blade, for example to an extent required to ensure that the mixing vane is fully immersed in the material held in the volume between two turns of the screw. The greatest impact of the mixing vane will typically be at the deepest part of the material in the volume between two turns of the screw, since this is where larger and heavier elements of the material will gather.

The height of the mixing vane, i.e. the extent of the mixing blade from the wall of the drum toward the centre of the drum may be at least 30% of the expected level of material in the drum, for example 40% of this level or more. The screw blade may typically not extend fully across the width of the drum and hence there may be a hole along the centre of the screw blade at the centre of the rotating drum. The extent of the screw blade is discussed in more detail below. The height of the mixing vane may be at least 20% of the height of the screw blade, for example at least 30% of the height of the screw blade. It is preferred that the mixing vane is fully immersed when it is with the deepest part of the material held in the drum and hence the height of the mixing vane may be less than the expected level of the liquid, such as 80% or less of the height of the liquid. With typical levels of liquid in devices of this time this may require a vane with a height of less than 70% of the height of the screw blade, optionally less than 60% of the height of the screw blade. Possible dimensions for the screw blade discussed in more detail below.

The mixing devices may comprise fluid inlets for the addition of fluid to the mixture within each volume between turns of the screw. The use of fluid inlets allows for the ratio of materials to be adjusted, for example by adding diluents or additional reagents to the materials within the rotating drum. Preferably there are fluid inlets in sufficient numbers and with suitable spacing to allow for one or more fluid inlet(s) for each turn of the screw. In this case fluid can be added to the original raw materials during each turn of the screw thereby increasing the amount of added fluid compared to the amount of the original raw materials as the material that is being mixed passes lengthwise along the drum. Each of the plurality of mixing devices may comprise a fluid inlet, or alternatively there may be multiple types of mixing devices of which only some of the plurality of mixing devices comprise a fluid inlet. The fluid inlets may advantageously be combined with mixing vanes, optionally with the fluid inlets opening into the drum at a surface or an edge of the mixing vane. In one example each of the mixing devices comprises a mixing vane having a ramp surface as described above, and also having one or more fluid inlets at a trailing edge of the ramp surface, i.e. at the furthest point of the ramp from the screw blade.

The apparatus may be arranged for the introduction of liquids into the material in the drum via the fluid inlets, for example the addition of reagents to change the characteristics of the material in the drum. The reagent may be an acid, a base, water, an organic solvent, or a solution such as water containing salt or buffer for example. The apparatus may be arranged for the introduction of gases into the material in the drum via the fluid inlets, for example the introduction of inert gases in order to remove oxygen and other reactive gases from the material being processed. The apparatus may include a source of fluid for introduction into the drum, this source hence comprising a reservoir of a liquid or gas such as those described above.

The fluids introduced by the fluid inlets may be at an elevated or lowered temperature compared to the temperature of the materials within the drum. In this way the addition of fluids by the fluid inlets can both prompt mixing of the materials within the drum and also adjust the temperature thereof. For example, hot water could be added to increase the temperature to prompt an enzymatic reaction in later parts of the drum apparatus or in a subsequent processing area, or a hot gas could be bubbled through the material for the same purpose. Alternatively, cold water or a cold gas could be introduced to reduce the temperature, for example to cause an enzymatic reaction to cease.

The apparatus may be arranged to supply fluid to the fluid inlets under pressure so that the fluid jets out of the fluid inlets into the material within the drum. This can aid mixing of the material as well as encouraging any reaction that might be intended to occur based on introduction of the fluid. The fluid inlets may include groups of fluid inlets at locations spaced apart along the screw blade, and thus each mixing device may comprise multiple fluid inlets, with multiple mixing devices being spaced apart around the extent of the screw blade. In the example where fluid inlets are combined with mixing vanes then there may be multiple fluid inlets at each mixing vane, such as a plurality of fluid inlets along a trailing edge of the ramp surface of the mixing vane.

It is advantageous for the apparatus to be arranged so that the supply of fluid via the fluid inlets into the drum can be controlled. Thus, the apparatus may include fluid flow control devices for controlling the rate of flow of fluid through the fluid inlets and in particular for allowing and preventing flow. For example, the apparatus may include valves for controlling flow to each fluid inlet or to groups of fluid inlets. In this case it is preferred for a controller to be provided that is arranged to permit flow through fluid inlets that are immersed within the material that is being mixed, and to prevent flow when the fluid inlets are not within the material that is being mixed. Thus, flow would be enabled when the fluid inlets are at their low point in rotation of the drum and within the level of the material that is being mixed within the drum, whereas flow would not be allowed when the fluid inlets are at higher points during rotation of the drum when they are above the level of the material that is being mixed. In one example the controller is linked with sensors allowing for rotation of the drum to be monitored, such that fluid inlets are only permitted to supply fluid when they are at a position where immersion within the material to be mixed is expected. Alternatively or additionally the controller may comprise switching devices located adjacent to the expected level of material within the drum, such that individual fluid inlets are activated and deactivated as they pass the switching devices and enter or exit the material at the base of the drum.

Each of the fluid inlets may be connected to pipework for supply of fluid from a source of fluid to the fluid inlet. This pipework may advantageously be located toward the centre of the drum, thereby minimising the risk of contact of the pipework with the material that is being mixed within the drum. This could cause corrosion or fouling of the pipework or of the mixture within the drum. Alternatively the pipework may be on the outside of the drum and optionally may connect to the mixing devices by passing within the body of the screw blade, thereby avoiding any contact with the material within the drum. It is preferred for the connections allowing for passage of fluid into the drum from the source of fluid to be located at a centre of the rotating drum, for example at one end or at both ends of the drum. In this way fluid can be passed through a turret type connection allowing for relative rotation, but not needing to cope with translation movement of the two parts of the connection.

The mixing devices may alternatively or additionally comprise one or more of: vanes, paddles, scoops or ridges in the wall of the drum, moving parts attached to the drum or the screw blade (e.g. rotors) with passive or active movement, and/or other static or dynamic mixing devices.

The screw blade is a helical screw blade and hence describes a spiral along the inside of the rotating drum. The screw blade may have a constant pitch along the length of the drum, or there may be a change in pitch of the screw blade between the inlet and the outlet, wherein the pitch of the helical screw blade is the height of one 360 degree helix turn. In one example the pitch of the screw blade may increase between the inlet and the outlet so that there is a larger pitch at the outlet than at the inlet. This means that the volume of the chamber is formed between turns of the screw blade will increase from the inlets to the outlet, and this can advantageously be used to compensate for the addition of fluid to the material within the drum as it passes along the drum.

As noted above the screw blade preferably extends from the inner surface of the outer wall of the drum toward the centre of the drum but does not fully fill the drum, i.e. there is an opening along the centre of the drum. This can allow for access for maintenance as well as during manufacture, whilst also enabling easier cleaning of the device since there are fewer fully enclosed chambers. The screw blade may extend from the wall of the drum inward for at least 50% of the radius of the drum, for example at least 60% or about 70% of the radius of the drum. The size of the mixing vanes relative to the size of the screw blade has been discussed above. The volumes formed between adjacent turns of the screw blade may be open to the hole at the centre of the drum, or alternatively these volumes may be closed, for example by a cylindrical body along the centre of the drum in that is fixed to the inner edge of the screw blade, preferably in a watertight fashion. This can allow for greater volumes of material to be held without risk of the volume spilling between adjacent turns of the screw blade, as well as allowing for a smaller headspace and potentially greater control of the atmosphere within the headspace. The headspace may comprise a low-oxygen or inert atmosphere, for example.

The inlet to the rotating drum and the outlet from the rotating drum may be at longitudinal ends of the drum. The inlet may comprise an opening at an inlet end of the drum, with an inlet pipe passing through the opening and allowing for material to be fed into the chamber formed between the first and the second turns of the screw. If the screw blade has a sufficiently large opening at the centre of the drum then material can be fed in from the inlet without any need for modification to the screw blade shape. The outer part of the end of the drum is preferably enclosed so that material fed into the drum cannot flow out from the inlet end of the drum. Thus, in the case of a cylindrical drum the inlet end of the drum may comprise an enclosed outer part with an open inner part, hence taking the form of a disc over the end of the cylinder with a hole at the centre of the disc. The central hole can receive the inlet pipe and also may receive pipework for supply of fluid to fluid inlets included as part of the mixing devices.

The outlet may comprise an opening at an outlet end of the drum, for example the outlet end of the drum may be fully open. This enables the material within the drum to exit the drum once it passes out of the final turn of the screw blade. The outlet may include a hopper or similar to receive material that exits the drum and guide it to the next stage of processing. This may, for example, be a further stage of enzymatic processing, or alternatively if the material that exits the drum is an end product then the next stage may be packing of the product. Since the material in the drum is conveyed via the screw blade then the geometry of a helical screw blade means that if the blade simply terminates without any modification to the form of the final turn(s) of the screw blade then the material will not flow continually out of drum but instead the flow rate will fluctuate. This uneven flow may not be a problem in some circumstances since there may be a possibility to use a hopper or the like as a buffer to gather the material and ensure a continuous flow can be passed to the next stage of processing. However, in some cases it is required to provide a more even flow rate from the outlet of the drum.

In order to provide a more even flow rate from the outlet of the drum then the drum and/or the screw blade may be provided with outlet features during the final turn(s) of the screw blade. The screw blade could be reduced in size toward the outlet end in order to allow for flow of material to spill over the blade and hence exit the drum more evenly. However for materials that are not homogeneous and, for example, include liquid matter as well as solid particles such as bone then this can result in the liquid matter exiting the drum evenly whilst the solid particles, which will settle toward the lower part of the drum and hence not spill over the blade, will still exit at an uneven rate.

An alternative approach is to include holes in the wall of the drum and/or in the surface of the screw blade during the final turn of the screw blade in order to reduce the fluctuations in the flow rate. Holes in the drum wall might require a complicated arrangement to catch the flow from the outlet, but could be beneficial for a relatively non-viscous and homogeneous material. It is also possible to use holes in the wall of the drum to separate liquid and smaller particles, with larger particles exiting the drum from the end of the drum. In this way the rotating drum can be used as a separator.

In one example, holes are provided with openings through the final turn of the screw blade in order to provide for fluid communication between the volume formed between the final and the penultimate turns of the blade and the outlet end of the rotating drum. The holes may be located at the outer perimeter of the screw blade close to the wall of drum and/or at spaced apart locations across the width of the screw blade. These holes may for example be placed in spaced apart locations covering a similar extent of the screw blades to the extent of the mixing vanes. The use of holes in the screw blade can even out the flow rate whilst also ensuring that there is even flow for all parts of the material even if there is a non-homogeneous mixture of, for example, liquid and solid matter. This is since the holes toward the outside of the screw blade, i.e. closest to the wall of the drum, will allow for particles that have settled under gravity to pass through, as well as allowing smaller particles and liquid to pass through. Where the rotating drum is intended for use with materials including solid particles then the size of the holes should be set based on the size of the particles so as to avoid unwanted clogging of the holes.

The holes may be of adjustable size, for example using sliding plates or interchangeable plates. This can allow for adaptation of the rotating drum for differing volumes of material, for differing sizes of solid particles and for differing characteristics of the mixed material, such as solid/liquid ratio, viscosity and so on.

The total area of holes should preferably be sufficient to allow for all of the material within the chamber formed between the final and penultimate turns of the screw to flow out toward the outlet end of the drum through the final turn of the screw blade during one turn of the drum. This would allow for an even flow rate of material out of the outlet from the drum. For typical applications this can be achieved by a total area of holes beneath the expected level of material in the drum that is in the range of 40-200 $cm^2$, which can be roughly equated to 180-850 $cm^2$ of holes spaced about the circumference of the final turn of the screw blade, assuming that the final turn is open for 90° of the perimeter of the drum, and thus that the holes are spread over 270° of the perimeter. This total size for the holes may be in the context of a drum with diameter in the range 1 to 5 m and overall flow rates in the range of 1000 to 6000 litres per revolution of the drum, i.e. a volume of material of 1000 to 6000 litres held between each pair of turns of the screw blade.

It should be understood that the requirement for a horizontal extent of the length of the drum and the axis of rotation of the drum is in order that the material within the drum will gather at a lower part of the drum under the action of gravity in order to thereby enable the action of the screw blade to convey the material along the length of the drum whilst also mixing it in conjunction with the mixing devices. It is not necessary that the length of the drum and the axis of rotation of the drum be completely horizontal, instead they need to extend in a horizontal direction. Thus, the drum could be set at an incline in order to also convey the material within the drum vertically upward or downward as well as horizontally, provided that the incline is not so much that the material would spill over the screw blade. The incline may for example be within 20 degrees of horizontal. In this way the rotating drum apparatus can be used in a similar manner to an Archimedes screw and convey material vertically and horizontally as well as mixing it. In the case where the inlet of the drum is higher than the outlet of the drum then the weight of the material in the drum may be used to aid rotation of the drum. This might advantageously allow the load on a motor or other drive device for rotation of the drum to be reduced. Having the inlet of the drum higher than the outlet of the drum may assist addition of fluid through the fluid inlets in the mixing devices, under the influence of gravity.

The rotating drum apparatus may include a drive device for propelling rotation of the drum, for example a motor attached through suitable gearing to the drum. The rotating drum apparatus may include supports for holding the drum and permitting rotation of the drum, for example supports incorporating bearings. The rotating drum might be held by roller bearings supporting its outer surface, or alternatively the rotating drum might be held via a shaft reported on journal bearings or the like.

The main body of the rotating drum can advantageously be a cylinder shape, although it will be appreciated that other tubular shapes might be used. An outer perimeter that is circular is generally straightforward to manufacture and could easily be supported for rotation, for example by roller bearings supporting the outer surface of the drum itself. A circular drum also reduces turbulence within the drum itself during rotation, and this can be an advantage for certain types of process. Alternatively, a noncircular drum for example a hexagonal or octagonal prism could be used. A non-circular drum may provide advantages in terms of mixing when a greater degree of turbulence is required.

In one example the drum is arranged to provide a processing capacity of 5 m$^3$ per hour or above, for example about 7 m$^3$ per hour, or in other situations about 30 m$^3$ per hour, or above. The diameter of the drum may be at least 2 m, for example 2.5 m to 3.5 m. The rotating drum may be arranged so that time taken for the raw material to pass along the extent of the drum is at least 15 minutes, or at least 20 minutes, for example the time taken may be about an hour or more. This allows for sufficient time for reactions to occur and/or for reagents to contact with all of the raw material. The length of the drum between the inlet and the outlet may for example be 3 m or more, for example 5.5 m or above 10 m. The inlet and the outlet may be at the ends of the drum. The diameter of the drum, the length of the drum and the speed of rotation of the drum may be set so as to provide a processing capacity as set forth above.

In one example the length of the drum is 11.75 m, the diameter of the drum is 3.5 m, the screw blade extends by 1.25 m into the centre of the drum from the outer wall and the mixing vanes have a height of 0.5 m. In this example there are five mixing vanes for each turn of the screw blade and there may be five fluid inlets spaced apart along the extent of the trailing edge of the mixing vane. This drum can be operated to process about 30 m$^3$ of material an hour in the form of 15 tonnes of raw material and 15 tonnes of water, with the travel time from the inlet to the outlet being about 1 hour.

A second aspect of the present invention provides a method of mixing and/or processing materials, optionally for enzymatic processing of organic molecules, preferably in a continuous flow process, the method comprising: feeding materials requiring mixing and/or processing into a rotating drum via an inlet a first point on the drum, the rotating drum being arranged with the length of the drum and the axis of rotation of the drum extending along the horizontal; rotating the drum and thereby mixing the materials whilst conveying them lengthwise along the drum using a screw within the drum, wherein the screw includes a helical blade extending along the length of the drum with the outer edge of the helical blade being fixed to the inner surface of the drum such that material can be conveyed and mixed in separated volumes between each turn of the screw; and discharging materials after mixing and/or processing from an outlet at a second point along the drum; wherein the rotating drum incorporates a plurality mixing devices for promoting mixing of the material in each of the separated volumes of material as the material is conveyed along the screw, wherein the plurality of mixing devices are spaced apart along the blade of the screw, and wherein there is at least one mixing device for each turn of the screw.

The method may for example be a method of mixing and/or processing materials for hydrolysis, such as for enzymatic processing. The method may alternatively be for other mixing and processing applications, as discussed above. The method may include using a rotating drum with any or all features as discussed above in relation to the first aspect. In particular, the method may include using mixing devices as discussed above, which may be mixing vanes and/or fluid inlets as described above. The method may include processing separate batches of material in each volume between adjacent turns of the screw.

Where fluid inlets are used as some or all of the mixing devices then the method may include introducing fluids into the material, for example introducing liquids or gases as mentioned above. The method may include heating or cooling the material in the drum by introducing fluid at elevated or lowered temperature.

The method can include controlling the supply of fluid via the fluid inlets so that the fluid is only supplied when the fluid inlets are immersed in the material in the drum. This can be done using features as discussed above, for example by controlling the flow of fluid according to the position of the respective fluid inlets in the drum.

The rotating drum apparatus or the method described above may be utilised as a part of an enzymatic processing plant or in a method of enzymatic processing, preferably as a part of a continuous flow process or alternatively as part of a non-continuous batch-flow process. The enzymatic processing may be enzymatic hydrolysis. The reference to a continuous flow process is intended to cover a process where the flow through the processing plant occurs in a single pass, without repeated circuits or batch-wise processing, with the reaction mixture entering the processing plant continuously and the product of the reaction exiting the processing plant continuously. Depending on the nature of the reaction there may be further raw materials added continuously partway through the process and/or products may be removed continuously partway through the process, for example oil soluble components may be continuously removed via a separator and so on. It will of course be understood that the optional feature of a fluid introduction system in the proposed apparatus can advantageously be used to add further fluid raw materials during the processing of the raw materials, for example by adding water during a hydrolysis process.

The enzymatic processing plant may comprise a enzymatic processing plant, preferably a continuous flow-based enzymatic processing plant, for enzymatic processing of organic molecules comprising: one or more enzymatic processing area(s), wherein the enzymatic processing area(s) comprise(s) a rotating drum apparatus as described above and optionally a turbulence-generating pipe with a repeatedly changing centre-line and/or a repeatedly changing cross-section, for generating turbulence to mix a reaction mixture and prevent sedimentation of particles as the mixture is flowing through the enzymatic processing area, and wherein the enzymatic processing plant and the enzymatic processing area are arranged such that the reaction mixture is subjected to turbulence and/or mixing within the enzymatic processing area of the rotating drum and/or the turbulence generating pipe for a reaction time of 15 minutes or more.

The optional features of the invention also extend to the equivalent method, i.e. a method of enzymatic processing, preferably continuous flow based, of organic molecules comprising: passing a reaction mixture through enzymatic processing area(s) including a rotating drum apparatus as described above and optionally through a turbulence-generating pipe, the turbulence-generating pipe having a repeatedly changing centre-line and/or a repeatedly changing cross-section, the turbulence generated by the turbulence-generating pipe being used to mix the reaction mixture and to prevent sedimentation of particles as the mixture is flowing through the turbulence generating pipe, wherein the reaction mixture is subjected to turbulence and/or mixing within the rotating drum apparatus and/or the turbulence generating pipe for a reaction time of 15 minutes or more.

In some cases a rotating drum as described above will perform better than a turbulence generating pipe, for example when the material to be processed has larger solid particles, a higher granularity, less liquid content and/or higher viscosity. The rotating drum can also provide for increased capacity and higher throughput in some situations. However in other cases the turbulence generating pipe can have advantages, since there are no moving parts and turbulence can be generated with reduced shear forces. It is envisaged that the combination of both types of device, or the ability to build a processing plant by selecting from the different types of device, will provide advantages by allowing the best selection to be made for most effective processing at a given stage of the process.

By the use of a turbulence generating pipe having a repeatedly changing centre-line and/or a repeatedly changing cross-section then turbulence is generated without the need for mixing mechanisms with moving parts or for static mixing elements of the type shown in EP-B-0566877. Mixing by turbulence in the pipe has an important advantage compared to stirring or static mixers as in the prior art; the mixing forces are distributed throughout the entire bulk. This reduces both stress concentration and formation of zones with poor mixing.

Moreover, prior art using mixing elements in flow pipes such as those in EP-B-0566877, or even prior art using corrugated pipework as in U.S. Pat. No. 4,126,517, does not allow for the continuous flow of heterogeneous biological substrates while maintaining thorough mixing for extended periods of time without clogging or sedimentation of solid particles. It is important to allow for long reaction times of at least 15 minutes and preferably longer, for example 20 minutes or more, 30 minutes or more, or even longer reaction times as set out below. The reaction times can be achieved by a combination of slow flow rates and pipework of sufficient length, again as discussed below. In the prior art referenced above the flow rates are too fast and the pipework is too short for the required reaction times in a continuous flow process.

As a result of turbulent flow through the turbulence-generating pipe and/or the mixing within the rotating drum apparatus, the reaction mixture is mixed and maintained as a homogenous mixture through the process. The turbulence also reduces the risk of sedimentation. Depending on the actual particle composition of the feedstock and the flow velocity then the turbulence can entirely prevent the heavier phases of the reaction mixture from settling.

Whilst a degree of turbulence is important for mixing the reaction mixture, it is also desirable to reduce (and ideally to minimise) the generation of shear forces in the pipe. Shear forces are caused by a fluid velocity that is too high, and can contribute towards the production of emulsions, which is undesirable.

Avoiding or reducing the formation of emulsions is an important consideration in enzymatic processing systems (for example, hydrolysis of protein/lipid mixtures). Emulsions block enzymatic access to parts of the feedstock trapped in emulsions and thus reduce the efficiency of enzymatic processing. Furthermore, the problem with emulsions extends to the separation stage. In emulsions, lipids may be tightly associated with water-soluble components such as peptide material which mechanical separators are unable to separate. Thus the result can be poor separation with, for example, lipid in the protein phase and/or protein in the lipid phase. Emulsions can be taken out by filtration at a later stage, but the emulsified components still cannot be recovered and combined with the non-emulsified fractions. That is, without specific equipment it is not possible to separate water-soluble components from the emulsion to recombine them with the non-emulsified water-soluble fraction, and nor is it possible to separate lipids and lipid-soluble components from the emulsion to recombine them with the non-emulsified lipid and lipid-soluble fraction.

It will be appreciated from the foregoing that the challenge is to obtain good mixing of the reaction mixture, without producing emulsions. Additionally, a minimum flow velocity is required to prevent solid particles from clogging the pipe. The proposed turbulence generating pipe using repeatedly varying cross-section and/or centre-line is able to generate turbulence at lower flow velocities and with reduced shear stresses compared to prior art static mixers and the like. By combining this type of a pipe with long reaction times and a continuous flow process it is possible to effectively perform enzymatic processing that is either not possible with the prior art, or that requires complex and hard to clean equipment, often restricted to batch processing.

The turbulence-generating pipe may be a tube, a hose, or the like. It may be rigid or flexible. The enzymatic processing area may be made up of a single pipe such that the reaction time occurs entirely within one turbulence generating pipe. Alternatively the enzymatic processing area may be made up of multiple turbulence generating pipes coupled together. In the discussion below the pipe is generally discussed as if it is a single pipe, but this should be taken to also encompass multiple pipes coupled together, for example multiple similar sections with similar variations in cross-section and/or centre-line to produce the required turbulence.

Example implementations may include providing a stacked, coiled and/or nested arrangement of pipework with the turbulence generating elements in order to allow a significant length of pipe to be accommodated in a relatively small space. There may, for example, be a series of interconnected horizontal layers, preferably with a downward flow, i.e. towards layers below.

Turbulence at low fluid velocity in the turbulence-generating pipe, for example in a corrugated pipe, may be due to changes in cross-section area. When the fluid flows through an expansion, a negative pressure occurs at the wall. The pressure gradient forms random disruption in flow patterns similar to turbulence in a smooth pipe. The same mechanism is present even when the cross-sectional area is constant, but the pipe has bends, a cross-section which changes shape, or a helical shape, because the fluid flowing along the wall experiences expansions along the path.

Compared to a smooth straight pipe of equal diameter, turbulence can be generated at a lower fluid velocity when a turbulence-generating pipe is used. The possibility of turbulence at lower fluid velocity leads to dramatic energy savings, as flow resistance is proportional to fluid velocity to the second power. The characteristics of the turbulence-generating pipe may lead to some extra flow resistance compared to a smooth pipe of equal diameter, but not enough to offset the savings resulting from the ability to run at a reduced running speed. In addition, a lower velocity gives the additional practical advantage of a shorter tube for a given hydrolysis time.

The turbulence generating pipe may be arranged to produce turbulence more easily than pipes without the claimed repeating changes in cross-sectional area and/or centre-line. Conveniently, the turbulence generating capacity of the pipe may be defined with reference to a threshold Reynolds number, above which there will be turbulent flow. In a simplified model (fluid flowing through a straight pipe with constant round cross-section and constant fluid properties) turbulence in a pipe may be quantified by the dimensionless Reynolds number, Re, which is defined as:

$$Re = \frac{v\rho D}{\mu} \quad \text{Equation 1}$$

Here, v is the mean velocity of the fluid, ρ is the density of the fluid, D is the diameter of the pipe μ is the viscosity of the fluid. The Reynolds number can be interpreted as the ratio of inertial forces to the viscous forces. It will be appreciated that as the viscosity increases or the density decreases then the flow speed must increase to maintain a set level of Reynolds number for the flow. Thus, with the same pipe geometry different flow speeds may be required to achieve turbulence with different feedstocks, or alternatively the same flow speed may be used if the geometry of the pipe is adjusted to increase the severity of the turbulence generating features.

For a straight pipe with constant round cross-section, the flow is assumed to be turbulent above a Reynolds number of 2300. For turbulence-generating pipes as described herein the transition from laminar to turbulent flow occurs at a lower Reynolds number.

Balancing the different requirements, e.g. the need for turbulent flow and sufficient drag forces to avoid sedimentation, but at the same time the slowest possible velocity in order to reduce energy consumption and tube length, gives a preferred range of Reynolds numbers. Preferably, flow of the reaction mixture within the turbulence-generating pipe is turbulent at Reynolds numbers of less than 1000, optionally at Reynolds numbers of less than 800, and optionally at Reynolds numbers of less than 600. Thus, the turbulence generating pipe may be arranged to always produce turbulent flow when the flow has a Reynolds number above a transition value of less than 1000, optionally at Reynolds numbers of less than 800, and optionally at Reynolds numbers of less than 600. That is to say, with the preferred pipe laminar flow will only be possible below a transition value of less than 1000, optionally less than 800, and optionally less than 600.

A minimum flow velocity is necessary to avoid clogging the turbulence-generating pipe with solid, slow-moving, heavy particles in the reaction mixture. This can be understood by considering a solid particle that is too heavy to follow the fluctuations of the turbulent flow, and so slows down within the flow. To move the solid through the pipe the mean drag-forces from the fluid acting on the particle must be high enough. In example implementations the plant may be arranged to operate with a flow velocity of less than 2 m/s, optionally less than 1 m/s and optionally less than 0.5 m/s.

The average diameter of the turbulence-generating pipe and flow rate of the reaction mixture are selected to give sufficient turbulence and sufficient running speed, but avoiding formation of emulsions.

It will be appreciated that the specific diameter, flow-rate and process time will need to be adjusted depending on a number of factors, including the composition of the feedstock and the particular reaction mixture to be processed, as well as the desired end product.

The process time is at least 15 minutes and may be at least 20 minutes. Typically the process time (i.e. the time which the reaction mixture takes to traverse the enzymatic processing area) will be between 90 minutes and 30 minutes, more preferably between 80 minutes and 40 minutes, and most preferably, about 50 minutes. The process time may of course vary depending on the particular reaction concerned, including factors such as the composition of the feedstock, enzyme efficiency and concentration, temperature, pH, ion conditions and the flow rates used.

The length of the turbulence generating pipe can be calculated from the desired flow rate and process time. While the overall processing time required would determine the total tube length, it might in some cases be desirable to divide the tube, i.e. the processing area, into a series of two or more successive compartments with or without an intervening pumping mechanism, in order to adjust reaction conditions such as temperature, pH and ionic conditions or substrate velocity or simply to accommodate the flow length of pipe in a given installation space.

The length of the turbulence generating pipe (series of connected pipes) may be at least 50 m, optionally at least 100 m. As will be evident from the examples discussed below the length may be considerably longer than this. The nature of the proposed arrangement is such that it allows for flexibility in adding processing stages with additional pipework and so on and it is capable of accommodating very long reaction times in a single continuous process.

The cross-section is the section transverse to the primary flow direction. A "changing cross-section" refers to a cross-section that has a changing area, a changing shape, or both a changing shape and changing area along the primary flow direction, i.e. along the extent (length) of the pipe.

In the current context, "repeatedly changing" means that the turbulence-generating pipe has a first configuration (cross-section and/or centre-line) at one location along the pipe, and a second configuration (cross-section and/or centre-line) at a second location along the pipe, and the turbulence-generating pipe repeatedly switches from one configuration to the second, and back again, along the length of the pipe. Thus the turbulence-generating pipe may conceptually be considered as comprising a number of joined-up repeating units.

The number of repeating units is typically greater than 10, more preferably greater than 20, most preferably greater than 50. The frequency of repeated units may be in the range of 5 to 200 per meter, more preferably, 10 to 100 per meter. More preferably, the frequency of repeated units may be in the range of 25 to 75 per meter, and most preferably is in the range of 40 to 60 per meter.

The characteristics of the repeating units may be defined in terms of their depth (e) and width (p). The width, p, (or spacing, or pitch) of the repeating units is the distance between one point on the repeating unit and the corresponding point on the next repeating unit (analogous to the wavelength of a wave). The depth, e, is the perpendicular distance between the tangent to the extreme outermost point of the repeating unit and the tangent to the extreme innermost point of the repeating unit.

The ratio of p/e for the turbulence-generating pipe is preferably greater than 0.5, more preferably greater than 1, and most preferably greater than 2. The ratio of p/e for the turbulence-generating pipe is preferably less than 50, more preferably less than 25, and most preferably less than 10. The ratio of p/e for the turbulence-generating pipe is preferably in the range of 3 to 6.

As noted above, the cross-sectional area may change repeatedly. For example, the cross-section may decrease, then increase, then decrease again (i.e. the pipe may constrict, broaden and constrict), and so on, along the length of the pipe. The cross-section may maintain the same shape cross-section whilst periodically changing cross-sectional area, i.e. the pipe may be a corrugated pipe.

Where the turbulence-generating pipe has a changing cross-sectional area, the difference between the maximum cross-sectional area and minimum cross-sectional area may be between 20% and 3% of the average cross-sectional area, more preferably between 15% and 5% of the average cross-sectional area, and most preferably about 10% of the average cross-sectional area.

Alternatively, or in addition, the shape of the cross-section may change repeatedly. For example, the cross-section may change from a circle to an ellipse to a circle, and so on, along the length of the pipe. Other shapes may also be used for the cross section, such as polygonal shapes, Reuleaux polygons, ovals such as Cassini ovals, star shapes and so on. Preferably the cross-section does not have any sharp corners, especially internal corners. The cross-section may maintain the same cross-sectional area whilst periodically changing shape. Alternatively, the cross-sectional area may also vary.

The centre-line is the continuous line passing through the geometrical centre of the cross-sections along the length of the pipe. An unchanging centre-line, in the context of the present application, is one in which the centres of the cross-sections at either end of the pipe are joined by a straight line. A changing centre-line is one in which the centre-line does not follow such a straight line. Thus, the pipe may have multiple repeated bends. The pipe may have a helical shape, such that the centre-line is a helix.

Some or all of the bends may be 90° or greater bends, for example 180° bends, in order to run the pipe backwards and forwards through an installation space. These are preferably large radius bends (preferably having a radius of curvature of greater than 2 times the diameter of the pipe, 4 times the diameter of the pipe, or 6 times the diameter of the pipe, or greater). Use of such large radius bends reduces pressure loss within the pipe, and so reduces also the risk of clogging. However, large radius bends increase the volume of installation. The skilled person will appreciate that the radius of curvature of the bends may be chosen having consideration of the installation space available. Thus, in a small space (for example, on a ship) the bends may need to have a smaller radius of curvature compared to a similar system located in a large factory, for example.

Sharper bends may also be used if pressure loss and clogging is not a major issue. In practice, this may be for fluid without large solid particles (such that there is no danger of clogging) and low fluid velocity (which leads to low pressure loss).

Typically, the average diameter of the turbulence-generating pipe will be in the range of 20 mm to 200 mm, and preferably in the range of 40 mm to 100 mm, most preferably in the range of 50 mm to 90 mm. For example, the average diameter of the turbulence-generating pipe may be about 60 mm or about 80 mm.

If the pipe has a helical shape (such that the centre-line is a helix) then the pitch of the helical centre-line should preferably be in the range of 10 to 100 mm, more preferably in the range of 13 to 40 mm, most preferably in the range of 17 to 25 mm.

Providing a helical turbulence-generating pipe, as well as resulting in the generation of turbulent flow within the reaction mixture, also allows a longer flow length of turbulence-generating pipe to be fit within a smaller space. Here, the flow length is the length traversed by the flow through the helical turbulence-generating pipe, i.e. the length of the pipe if the helix were to be unwound and the pipe straightened out.

A section of smooth and/or straight pipe may precede or follow a section of turbulence-generating pipe or could be used in connection with bends of the tube. A smooth, straight pipe presents less resistance to the flow, and so results in reduced pressure loss, compared to a turbulence-generating pipe of equal length. If a smooth pipe is provided, the length of smooth pipe should be sufficiently small that the reaction mixture does not have time to separate out whilst traversing the smooth pipe.

It is particularly advantageous if the turbulence generating pipe is a corrugated pipe, and hence preferred arrangements make use of a corrugated pipe.

A corrugated pipe is a pipe, tube, or hose, etc. with a series of parallel ridges and grooves (alternating ridges and troughs) on its surface, wherein the ridges and grooves result in a varying cross-sectional shape and/or a varying cross-sectional area along the length of the pipe. The grooves and ridges can be formed in a circumferential (annular) pattern or run along the length of the pipe in a helical pattern (spiral) around the pipe. The helical pattern may have a single start, a double start, or multiple starts. The corrugation pattern forms the repeating unit for the turbulence generating pipe.

The ridges and troughs may have (approximately) the same shape, (that is, a trough is the mirror image of a ridge, or approximately so). The shape of the corrugations may be, or may approximate, a sin wave. In alternative preferred embodiments, the shape of the corrugations (viewed in cross-section) may resemble a plurality of perimeters of sectors of ovoid shapes (for example, ovals, circles, or ellipses) joined together.

The grooves and ridges should preferably have no sharp corners in the interior of the turbulence-generating pipe, for example the corners preferably have a radius of at least 3 mm or more, more preferably 6 mm or more. The grooves and ridges should preferably be formed without any sharp intersections between adjacent surfaces or planes in the interior of the turbulence-generating pipe, preferably with no intersections sharper than 90 degrees.

The corrugated pipe may straight, may be formed in a helical shape (as discussed above in relation to the first or second aspect), or may have multiple repeated bends (as discussed above in relation to the first or second aspect).

If the corrugated pipe has multiple bends or is formed in a helical shape, the bends or helical shape may be provided to facilitate further generation of turbulence within the corrugated pipe, or may be provided in order that a larger flow length of corrugated pipe may be provided in an installation space (as discussed above in relation to the first or second aspect). The corrugated pipe may be formed in a tight helix (similarly to the shape of a coil spring, for example). This may allow a larger flow length of corrugated pipe may be provided in an installation space. The helix may be substantially horizontal (that is, the coil axis is substantially horizontal), or substantially vertical (that is, the coil axis is substantially vertical). The helix may of course be provided in any orientation between vertical and horizontal.

The turbulence-generating pipe should be made of a suitable corrosion resistant material and may for example be made from stainless steel. In preferred embodiments the pipe may be made of a food grade acid resistant stainless steel, for example a suitable molybdenum alloyed stainless steel such as ANSI 316.

The turbulence generating pipe may include a layer of immobilised enzymes attached to the inner surface of the pipe. In such a case, the layer of immobilised enzymes is preferably provided in the system at a point downstream of a point at which solid components are separated out from the flow, such that the flow through the turbulence generating pipe may include a layer of immobilised enzymes is primarily a flow of liquid.

When the enzymatic processing is initiated, the viscosity inside the pipe may change and it may be desirable to divide the overall processing area into successive tube compartments with different diameters in order to maintain sufficient turbulent mixing and drag forces. Thus a first enzymatic processing stage of about 30 minutes to one hour (for example) may imply changes in the flow characteristics. This may be taken account of by having turbulence generating pipes of different designs and corresponding changes in flow velocity for different stages of the enzymatic processing.

From the foregoing, it will be appreciated that the proposed enzymatic processing provides a simple system with few moving parts to accommodate reaction times typical for industrial scale enzymatic processing of biological material, e.g. hydrolytic processing. The system may therefore have a lower weight compared to prior art systems arranged to process a comparable amount of reaction mixture, making it suitable for additional applications where a heavier system would not be acceptable. The system may also be easier to clean than prior art systems with active or static mixing components.

The enzymatic processing plant may include a mixing unit where water, raw material and enzymes are blended, in communication with the input of the enzymatic processing area. Correspondingly, the enzymatic processing method may include the step of pre-mixing the reaction mixture, prior to enzymatic processing.

The mixing unit may take the form of a reservoir in which the raw material, water and enzymes are combined. Provision of a mixing unit is advantageous as the reaction mixture is already crudely mixed (i.e. premixed, or partly mixed) by the time it reaches the enzymatic processing area. This reduces the period of time necessary for enzymatic processing, allowing a smaller length of turbulence-generating pipe (for a given flow velocity) compared to the case where the raw material, enzymes and water are provided in an unmixed state into the enzymatic processing area. Thus the plant is more suitable for use in an enclosed space, for example in a ship, such as a fishing vessel.

The mixing unit may be sealed (i.e. is not an open tank), and the pre-mixing may be carried out within a sealed atmosphere. This reduces the amount of oxygen to which the feedstock is exposed, and so reduced undesirable oxidation of components in the feedstock. Preferably the mixing tank does not have any significant headspace.

The enzymatic processing plant may include a first section of turbulence-generating pipe in which primary enzymatic processing (in which the enzyme catalyses a first chemical reaction) takes place and may further comprise a second section of turbulence-generating pipe configured to receive a flow of a new enzyme capable of catalysing a second chemical reaction, different from the first chemical reaction. The second chemical reaction may involve a different component of the reaction mixture from that involved in the first reaction. Furthermore, different types of enzymes may be used in different stages of the process.

For example, a first hydrolysis stage may treat protein components of the feedstock. After that stage, the oil-soluble fraction may be separated from the reaction mixture, and may subsequently be treated with lipases.

The second chemical reaction may involve the products of the primary enzymatic processing. An example is a second hydrolysis stage treating the water soluble fraction from a preceding first stage (treated with proteases) with other proteases.

Any transition from one enzymatic processing to another may be accompanied by adjustment of reaction conditions such as temperature, pH and ionic conditions. Injection points may be provided where the characteristics of the reaction mixture can be adjusted, for example for pH or ionic strength. In addition, the injection point may allow for the introduction of water. This may be necessary in case the enzyme is water soluble (and not oil soluble), but the fraction to be processed is oil-based. For the enzyme to act on the oil-based fraction, a suspension may be formed, allowing contact between the enzyme and oil-based fraction.

As an example, a first hydrolysis stage may make use of endopeptidase alcalase (Novozymes) which works best at a pH in the range of about 6.5 to 8.5 and a second hydrolysis stage may make use of acid protease A (Amano Enzyme Inc.) which works best at a pH of 2.5. Thus, the first hydrolysis stage is carried out at around neutral pH, whereas the secondary hydrolysis stage is carried out in acidic conditions.

In each section, one or more enzymes may be utilised at the same time. For example, in some embodiments proteases may be used together with other enzymes such as, for example, lipases and/or carbohydrases, during the primary enzymatic processing and optionally also or alternatively in subsequent enzymatic processing stages.

The enzymatic processing plant may include a section of turbulence-generating pipe which is configured to be heated to a temperature such that, in use, the enzymes are inactivated (deactivated, or denatured) by heat. For example, when processing fish material, it is typical to use a protease enzyme which operates optimally at 55° C. This particular protease may be inactivated by raising the temperature to about 95° C. However, it is not essential that an enzyme be deactivated prior to treatment with another enzyme.

From the foregoing discussion, it will be appreciated that it is a significant advantage for the proposed arrangement that the enzymatic processing, within what is effectively a single tube without moving parts, can be carried out at multiple temperatures. The temperature of the pipe may be controlled and adjusted by means of any suitable heat exchanger. For example the pipe may be surrounded by a heat exchange fluid, with the heat exchange fluid being flowed past the pipe and/or heated or cooled in order to provide a required temperature within the enzymatic processing area within the pipe. A tube-in-tube heat exchanger could be used. The heat exchange fluid could for example be steam or water.

The lengths of the respective sections may be chosen so as to provide the necessary processing time in each section.

The enzymatic processing plant may include a separator system. The separator system may be operable to separate water-soluble components from lipids, for example. The separator system may comprise a three-phase decanter operable to output a flow of oil (lipids, and oil-soluble components), a flow of water-soluble components, and a flow of sediment. The separator system may comprise one or more centrifuges to further separate components in the oil-soluble flow and/or components in the water-soluble flow. The separator system may also comprise one or more filters (molecular sieves or mechanical filters, for example).

The feedstock may comprise oil-based components, such as fish oils, fish liver oils, mammalian oils (for example, seal), crustacean oils (for example, krill) and molluscan oils (for example, squid), as well as oils present in marine and freshwater algae, yeast or oilseeds.

The enzymatic processing plant may be provided with a further section of turbulence-generating pipe configured to receive the output from the primary processing, for example the lipid flow and the addition of lipases to modify the lipids.

The enzymatic processing plant may be provided with a polisher for cleaning an oil-based component.

The enzymatic processing plant may be provided with a separator system and drier for separating and drying solid components of the reaction mixture. The solid components may for example be insoluble proteins, bone (comprising protein and/or minerals), shells of crustaceans (comprising carbohydrates and/or chitin).

Some form of separator system (for example, a filter) may be used to separate the insoluble proteins from the remaining solid components. The insoluble proteins and remaining solid components may then subsequently be treated separately (for example, in further enzymatic processing stages).

Any emulsified components present in the system may be separated from the main flow using a filter, and may also be included in the solid fraction to be dried in the drier.

When the feedstock contains fish material, for example, at least some of the solid components (which may also include emulsified components) may be dried to form bonemeal, or fishmeal, for example, which may be used in products such as animal feed or fertilizer.

The enzymatic processing plant may be provided with a further section of turbulence-generating pipe configured to receive at least some of the solid components and an enzyme for treating the solid components in an enzymatic processing step. For example, when processing crustaceans such as krill, the solid components will comprise chitin (from the shells of the crustaceans). This chitin may be treated with chintinases in an enzymatic hydrolysis step.

Thus the above-described components of the enzymatic processing plant may be provided as a modular system, i.e. a system having multiple stages, or multiple steps. Such a system may be configured to output a number of different products. In such a modular system, provision of a turbulence-generating pipe is not seen as essential, although it is advantageous. The turbulence generating pipe and/or the rotating drum apparatus, as well as more broadly the enzymatic processing area described above may advantageously be included as the enzymatic processing area described in the aspects below.

Thus, a further aspect of the present invention provides a method of manufacturing a modular enzymatic processing plant for enzymatic processing of a reaction mixture, the method comprising determining a required enzymatic processing process and manufacturing a suitable enzymatic processing plant from a kit of modular parts by providing:

a pump for pumping the reaction mixture through the enzymatic processing plant;

a first enzymatic processing area for performing a first stage of enzymatic processing, the first enzymatic processing area including a rotating drum as described above;

a separator system comprising a decanter for separating a flow of water soluble components, oil-soluble components and solid components;

the method optionally further comprising:

considering whether or not each of the following components are necessary for a processing plant capable of performing the required enzymatic processing process: a filter; a second enzymatic processing stage; a third enzymatic processing stage; a post-separator system stage; a flow division stage; a heat inactivation stage and a flow combining stage;

and, including the necessary components in the modular plant.

The method may include providing a second enzymatic processing stage. The second enzymatic processing stage may be provided downstream of the first enzymatic processing stage, and may be configured to be in communication with the first enzymatic processing area such that in use, the second enzymatic processing stage receives at least a portion of the reaction output from the first enzymatic processing area. The second enzymatic processing stage may include a turbulence generating pipe as discussed above, or some other apparatus, including perhaps a further rotating drum. In one possible example fish or shellfish such as crab or mussels are to be hydrolysed enzymatically. First they are crushed with shell on, for instance between rollers. Then the whole material is hydrolysed with an effective protease using the rotating drum, which can easily handle the mixture of liquid, solid and crushed shells/bone without risk of clogging. At the outlet of the drum the shells/bone are clean, and they may be sifted out by means of a filter device, and the liquid rich part of the material from the rotating drum is then further hydrolysed using the same or different enzyme(s) through the use of a corrugated pipe. This could be done to reduce peptide size, to modify taste and so on. Tailor-made enzymes can be used for many purposes in accordance with the user requirements.

The method may include providing a third enzymatic processing stage. The third enzymatic processing stage may be provided downstream of the second enzymatic processing stage, and may be configured to be in communication with the second enzymatic processing area such that in use, the third enzymatic processing stage receives at least a portion of the reaction output from the second enzymatic processing area.

The method may include providing a heat inactivation stage. A heat inactivation stage may be provided downstream of the first enzymatic processing stage, and/or downstream of the second enzymatic processing stage, and/or downstream of the third enzymatic processing stage. The heat inactivation stage(s) may comprise a turbulence-generating pipe configured to be heated to a temperature such that, in use, the enzymes are inactivated (deactivated, or denatured) by heat.

The method may further comprise considering whether or not each of the following post-separator system stages are necessary for a processing plant capable of providing the necessary processing: a further enzymatic processing stage, a drier or a polisher. The method may include providing a post-separator system stage.

The second and/or third processing stage(s), or further processing stage(s) may be provided downstream of the separator system, and may be configured to be in communication with the separator system such that in use, the second and/or third enzymatic processing stage receives one of the following output from the separator system: the flow of water soluble components, the flow of oil-soluble components, or the solid components. The method may include providing a turbulence generating pipe as described above as one processing stage and a rotating drum apparatus as described above as another processing stage.

The method may include providing a drier for drying solid components. The method may include providing a polisher for cleaning oil-soluble components.

The method may include providing a flow division stage at which the flow is divided into two or more flows. The plant may be configured such that, in use, the two or more flows are processed in different stages downstream, or one or more of the flows may be returned to an earlier stage.

The flow division stage may be provided after the first enzymatic processing stage, after the second enzymatic processing stage, after the third enzymatic processing stage, or after the separator system.

The method may include providing a flow combining stage at which, in use, a flow from downstream is combined with a flow earlier in the plant.

The flow combining stage may be provided before the first enzymatic processing stage, before the second enzymatic processing stage, before the third enzymatic processing stage, before the separator system, or before the drier.

The method may include providing an injection point prior to an enzymatic processing stage for introducing chemicals to modify reaction conditions within the stage. The injection point may be provided before the first enzymatic processing stage, before the second enzymatic processing stage, before the third enzymatic processing stage, before the separator system, or before the drier.

The method may include providing a heat exchanger for heating or cooling an enzymatic processing stage.

The method may include providing an enclosed mixing chamber upstream of the first enzymatic processing stage. The mixing chamber may be heated by a heat exchanger in order to bring the reaction mixture to a temperature suitable for optimal enzymatic action in the first hydrolysis stage. Alternatively or additionally, the reaction mixture may be brought up to (or close to) the required temperature by adding hot water to the feedstock. In embodiments where the enzyme is added directly into the reaction mixture in the mixing chamber, care must be taken that the enzyme is not deactivated (denatured) by the hot water, by keeping the temperature of the reaction mixture below the deactivation temperature. To avoid such a problem, the enzyme may not be added into the mixing chamber, but may instead be added to the reaction mixture through an injection point at the start of the first enzymatic processing stage. A rotating drum apparatus as discussed above may be used as the mixing chamber, with heating from outside of the drum and/or heating by adding hot water as the mixture is conveyed through the drum.

The method may include providing a filter for separating from the reaction mixture components with a given molecular size, or larger.

The invention also extends in a further aspect to a kit of parts for making an enzymatic processing plant for enzymatic processing of organic compounds in a reaction mixture, the kit of parts comprising: a pump for pumping the reaction mixture through the enzymatic processing plant; a first enzymatic processing area for performing a first stage of enzymatic processing; and a separator system comprising a decanter for separating a flow of water soluble components, oil-soluble components and solid components; and the kit of parts further comprising one or more of: a filter; a second enzymatic processing stage; a third enzymatic processing stage; a flow division stage; a flow combining stage; an injection point; a heat inactivation stage; a mixing chamber; a polisher; and a drier;

wherein at least one of the enzymatic processing areas comprises a rotating drum as described above in relation to the first aspect and optionally the preferred features thereof.

In preferred embodiments the kit of parts comprises parts selected in order to meet the requirements of the above method of manufacturing a modular enzymatic processing plant. As noted above, the kit of parts may include an enzymatic processing area with features as described above in relation to the earlier aspects of the invention.

A particular advantage of the aspects and preferred arrangements above is that the system may be operated as a closed system, meaning that oxygen within the system may be minimised or at least reduced compared to prior art systems. Advantageously, oxidation of any oil components may thereby be reduced. It is preferred for the closed system to have no open tanks and no open liquid surface (i.e. any tank such as the mixing tank preferably does not have any significant headspace). This is particularly convenient when using the turbulence generating pipe for the enzymatic processing area. When using the rotating drum, an inert atmosphere (or low-oxygen atmosphere) could be introduced in the headspace, for instance through the fluid inlets described above.

The apparatus or method of any of the embodiments above may be used on board a ship. Thus, in one example a ship may be fitted with the proposed enzymatic processing plant, and a method including carrying out enzymatic processing as described above may be carried out on board a ship. The turbulence-generating tube and/or the rotating drum can contribute to a reduction in size and weight of the apparatus required, which is a significant advantage for shipboard use. In addition, the apparatus or method for shipboard use preferably includes operating the system without any open tank or other open liquid surface. This provides further advantages since in general any open liquid surface should be avoided onboard a ship, due to the risk of sloshing and consequent instability of the ship. When a rotating drum is used for the enzymatic processing area onboard a ship, for instance in order to accommodate very large processing capacity, the distance from the substrate material at the base of the drum to the top of the screw blade may be increased or the volumes formed between adjacent turns of the screw blade may be enclosed, for example with a cylindrical body fixed to the inner edge of the screw blade as mentioned above.

Certain preferred embodiments will now be described in greater detail by way of example only with reference to the drawings, in which.

Figure 1A:
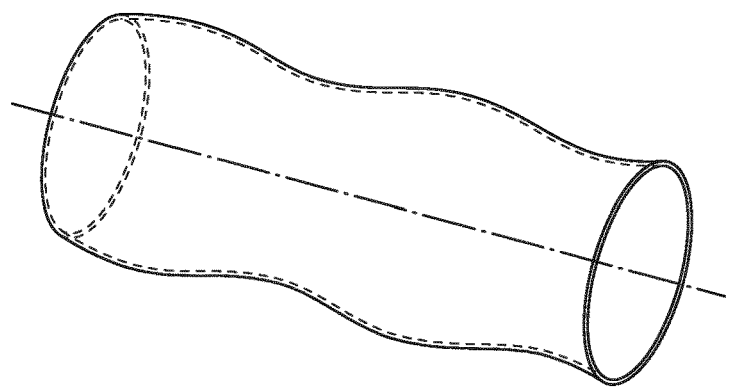
FIG. 1A shows a part of a corrugated turbulence-generating pipe.

FIG. 1A shows a part of a corrugated turbulence-generating pipe. The pipe has a diameter of about 60 mm, corrugation depth e of about 6 mm, and p/e of about 13. In such a pipe, turbulence occurs at Reynolds number above approximately 800.

Figure 1B:
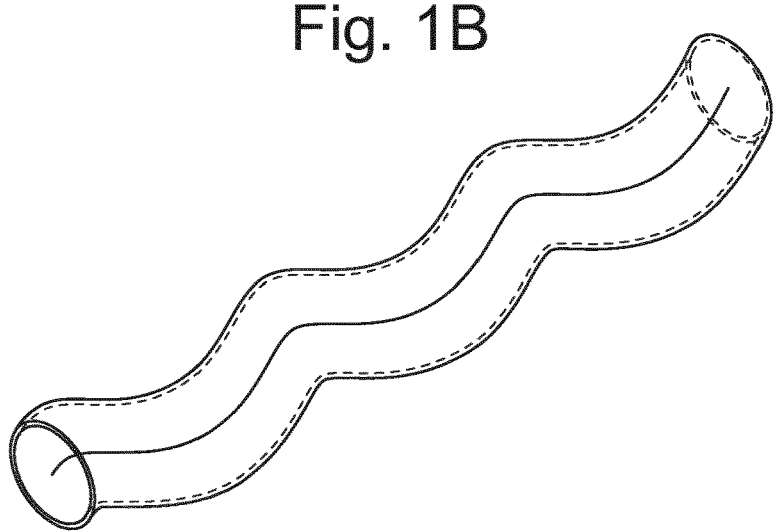
FIG. 1B shows a part of a helical turbulence-generating pipe.

FIG. 1B shows a part of a helical turbulence-generating pipe. The pipe has a diameter of about 60 mm. The pitch of the helical centre-line is 20 mm, and the radius of curvature of the helical centre-line is 1.5 mm.

Figure 1C:
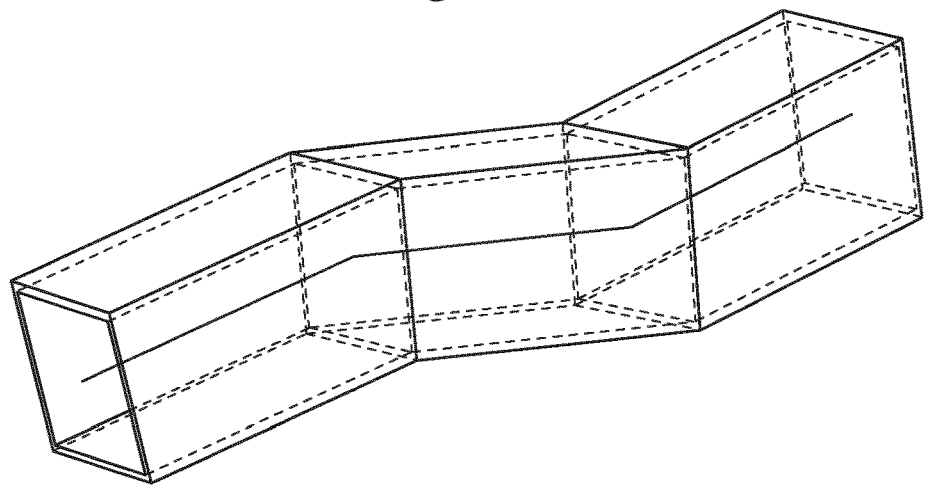
FIG. 1C shows a part of a turbulence-generating pipe having bends.

FIG. 1C shows a part of a turbulence-generating pipe having bends. The pipe has a cross-section that is square with sides of about 60 mm. The bends are at an angle in the range of 15° to 30°

Figure 1D:
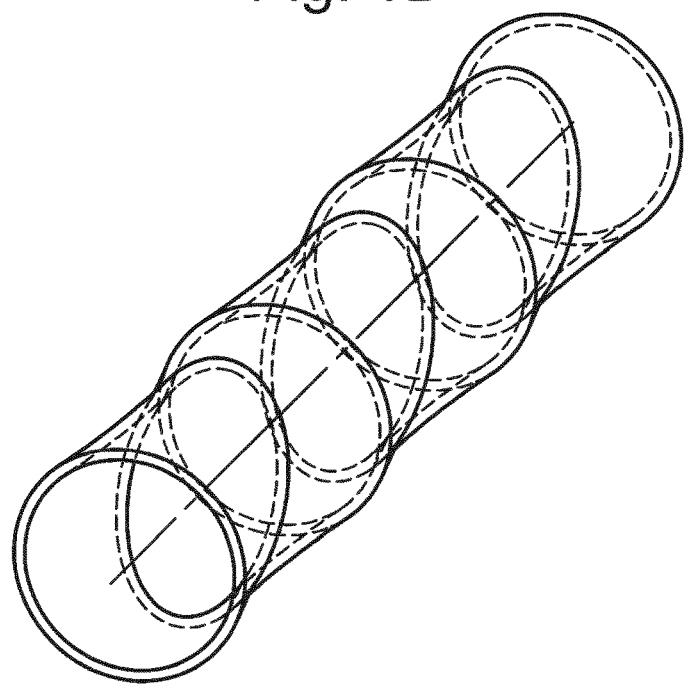
FIG. 1D shows a part of a turbulence-generating pipe having a changing cross-sectional shape.

FIG. 1D shows a part of a turbulence-generating pipe having a changing cross-sectional shape. The pipe changes from a circular cross-section to an elliptical cross-section. The cross-sectional area is about 2800 mm².

Figure 1E:
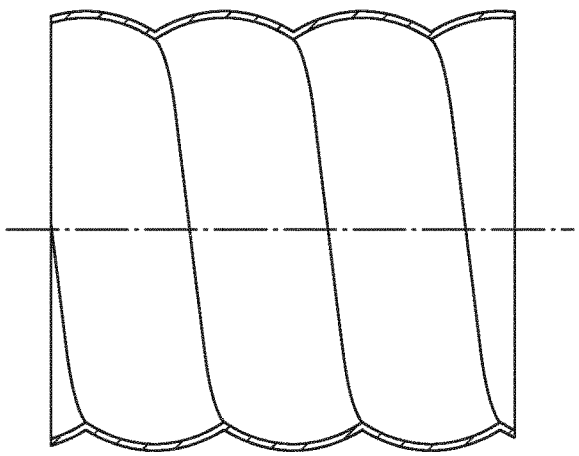
FIG. 1E is a cross-sectional view of a pipe with a helical corrugation pattern.

FIG. 1E is a cross-sectional view of a pipe with a helical corrugation pattern, the helix having a single start.

Figure 2:
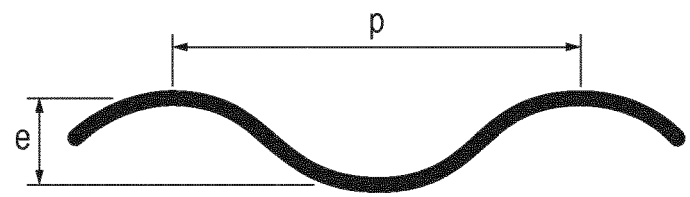
FIG. 2 shows the parameters of depth and width for a corrugated pipe.

FIG. 2 shows the pitch (width) p and depth e of corrugations on a corrugated pipe.

Figure 3:
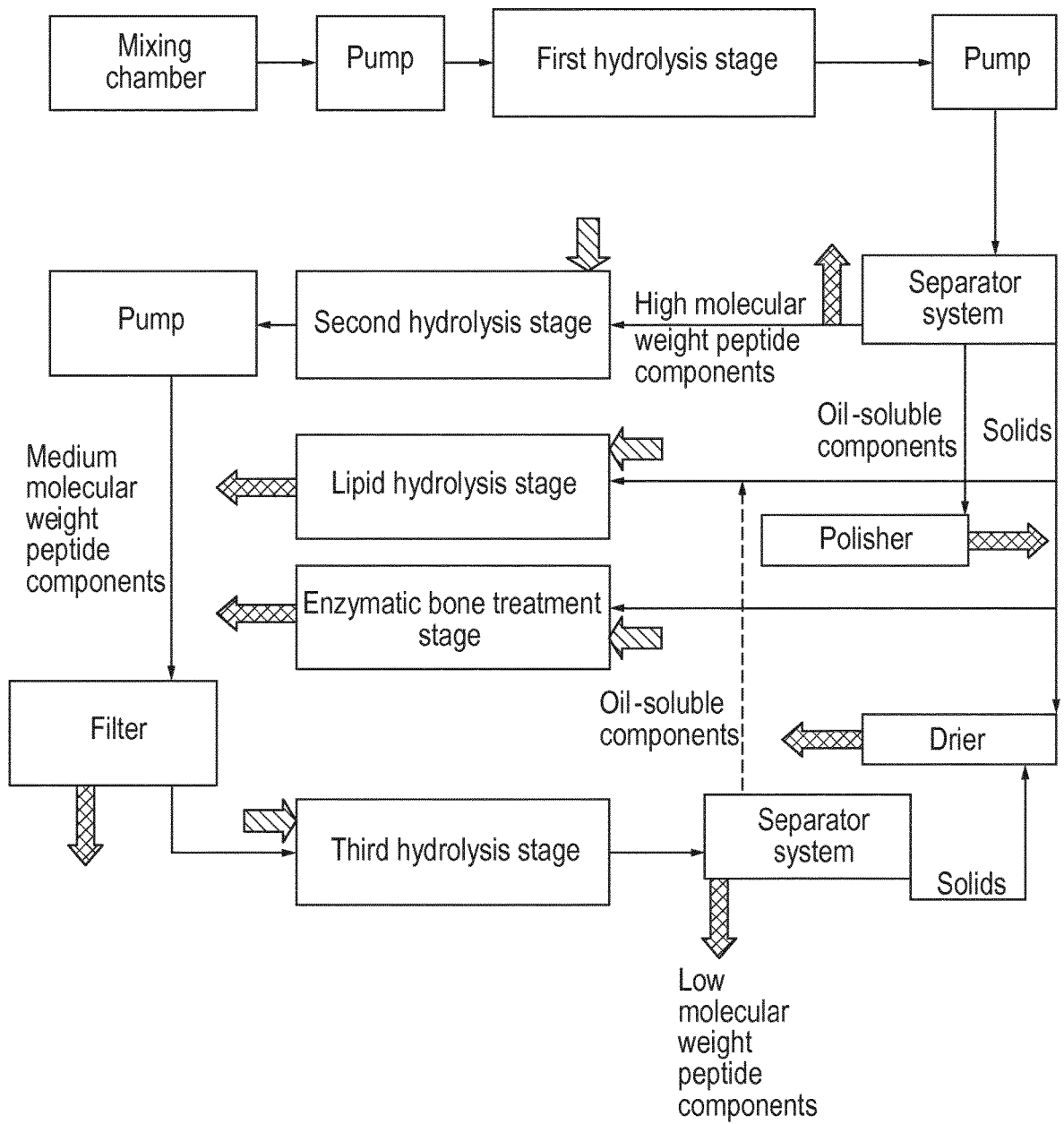
FIG. 3 shows a modular plant for enzymatic processing.

FIG. 3 shows a modular plant for enzymatic processing of organic molecules. In this case, the plant is for hydrolysis of protein in a protein-lipid mixture. The use of the plant for hydrolysis is exemplary and not limiting on the invention; it will be apparent that a similar apparatus could be used for any multi-stage enzymatic process. Further, in this case, the raw material processed by the system is fish. However, the use of the plant for processing fish is exemplary and not limiting on the invention; it will be apparent that a similar apparatus could be used with a different raw material. Further examples of processes making use of the proposed device are set out below. It should further be noted that although use of the rotating drum of FIGS. 4 to 7 within the plant of FIG. 3 is an advantageous use, the rotating drum may also be used for other types of processing as described earlier.

The particular enzyme (and hence reaction conditions) used in each stage will depend on the raw material and the products to be obtained, and can be chosen accordingly.

The plant of FIG. 3 may use only the rotating drum of FIGS. 4 to 7 as the apparatus for carrying out the various hydrolysis stages. Alternatively the turbulence generating pipe may be used. The rotating drum could instead or additionally be used as the mixing chamber for pre-mixing of the materials, either prior to hydrolysis in another rotating drum, or prior to hydrolysis in a turbulence generating pipe (or indeed hydrolysis in any known hydrolysis apparatus).

The plant in one example comprises a rotating drum as described below for pre-mixing the reaction mixture prior to injection into the first hydrolysis stage. Aside from an input for receiving the raw materials and an output for connection to the next section of the hydrolysis plant, the mixing chamber is sealed and preferably has an oxygen depleted headspace, for example an atmosphere of an inert gas such as nitrogen gas, so as to reduce the amount of oxygen which is brought into contact with the reaction mixture. This reduces oxidation of oils present in the feedstock. The rotating drum is heated by a heat exchanger, or alternatively the reaction mixture is heated after it exits the rotating drum in order to bring the reaction mixture to a temperature suitable for optimal enzymatic action in the first hydrolysis stage.

The fish material, water, and a protease are mixed and heated in the mixing chamber. After mixing, the reaction mixture is pumped by a pump into the first hydrolysis stage. Here, protein in the reaction mixture is hydrolysed to form high-molecular weight peptides. The first hydrolysis stage is a corrugated pipe having a mean diameter of 46 mm, with a plurality of 180° bends, with radius of curvature of 200 mm.

In the first hydrolysis stage, the reaction mixture has the following properties:
Density $\mu=1000$ kg/m³
Viscosity $\rho=0.02$ Ns
Reynolds number Re=800
Mean velocity v=0.35 m/s The volume flow rate for a given diameter is given by:

$$\dot{V} = \frac{\pi}{4} * D^2 * v \qquad \text{Equation 3}$$

For the parameter values given above, this gives a volume flow rate of 2.1 m³/h. The total length of the first hydrolysis stage is of the order of 1 km, and the processing time is of the order of 1 hour.

Towards the end of the first hydrolysis stage, the corrugated pipe is heated to a temperature hot enough to deactivate (denature) the protease.

The flow from the first hydrolysis stage is pumped using a pump to a separator system. The separator system comprises a three-phase decanter operable to output a flow of oil (lipids, and oil-soluble components), a flow of water-soluble components, and solid components.

The solid components from the separator system (primarily bone) are treated in two separate ways. A portion of the solids is passed to a drier (for example by a conveyor, not shown) and is dried to form fishmeal. The fishmeal is output as a product of the system (useful outputs of the system are shown as shaded arrows). A second portion of the solids is passed (for example by a conveyor, not shown) to a further enzymatic treatment stage for further treatment.

The further enzymatic treatment stage includes an input means for modifying the pH or ionic properties of the reaction mixture to suit the optimal operating conditions of the enzyme (shown as a hatched arrow). The product of the further enzymatic processing is output as a product of the system, after drying in a further drier (not shown).

The oil-soluble components from the separator system are also treated in two separate ways. A portion of the oil-soluble components is passed to a polisher (using a pump, not shown) which cleans the oil. The cleaned oil is separated into component parts using a centrifuge and filter (not shown) and the resultant components are output as products of the system. A second portion of the oil-soluble components is passed to a lipid hydrolysis stage (using a pump, not shown) and is treated with lipases. The lipid hydrolysis stage includes an input means (shown as a hatched arrow) for modifying the pH or ionic properties of the reaction mixture to suit the optimal operating conditions of the lipase. In addition, the input means allows for the introduction of water. This is necessary since lipases are water soluble (not oil-soluble). Thus, for the lipase to act on the lipids, a suspension may be formed, allowing contact between the lipase and lipids. Provision of a turbulence generation pipe which mixes efficiently but minimizes the formation of emulsions is useful in such a process. The option of providing a low-oxygen atmosphere in the headspace is a further advantage. The product of the lipase processing is output as a product of the system.

The water-soluble components from the separator system are also treated in two separate ways. A portion of the high-molecular weight peptide components are filtered out (using a filter, not shown) and are output from the system as a product. The remaining portion is input into a second hydrolysis stage.

The second hydrolysis stage includes an input means (shown as a hatched arrow) for modifying the pH or ionic properties of the reaction mixture to suit the optimal operating conditions of the second protease. The protease hydrolyses high-molecular weight peptide components to form medium-molecular weight peptide components. Towards the end of the second hydrolysis stage, the second hydrolysis stage is heated to a temperature hot enough to deactivate the protease.

From the second hydrolysis stage, a portion of the medium-molecular weight peptide components are filtered out using a filter and are output from the system as a product. The remaining portion is input into a third hydrolysis stage.

The third hydrolysis stage includes an input means for modifying the pH or ionic properties of the reaction mixture to suit the optimal operating conditions of the third protease (shown as a hatched arrow). The protease hydrolyses medium molecular weight peptide components to form low-molecular weight peptide components.

Towards the end of the third hydrolysis stage, the third hydrolysis stage may, if needed, be heated to a temperature hot enough to deactivate (denature) the protease.

From the third hydrolysis stage, the reaction mixture is passed to a separator system, which separates low-molecular weight peptide components from any remaining solids or oil soluble components. Any solid components are passed back to the drier (or the enzymatic bone treatment stage) and any oil components are passed back to the lipid hydrolysis stage (or the polisher). The low-molecular weight peptide components are output from the system.

The skilled person will appreciate that not all of these components are essential, and depending on the raw materials and desired end products, a combination of the elements of this system will be employed. In particular, the rotating drum could be used as an apparatus for handling one or more of the hydrolysis stages as well as for the mixing chamber.

Figure 4:
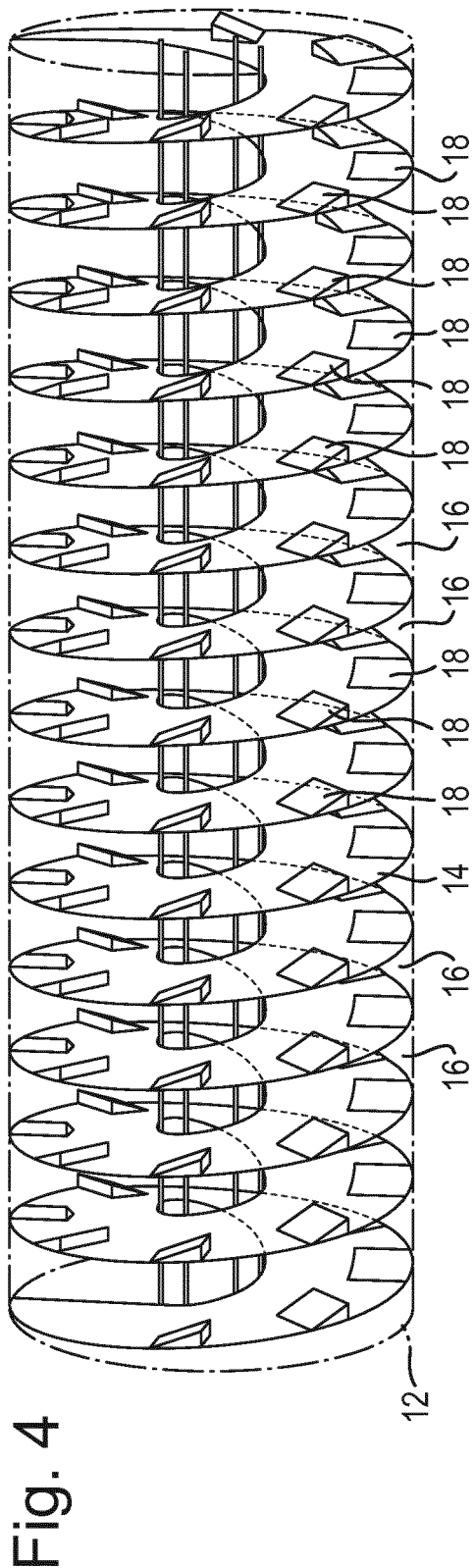
FIG. 4 illustrates a drum for rotation to mix material within the drum and convey the mixture along the length of the drum.

FIGS. 4 to 7 show a rotatable drum that can be used in a rotating drum apparatus for mixing and conveying raw materials, such as for mixing raw materials for hydrolysis as explained above. As can be seen in FIG. 4 the rotatable drum has a cylindrical shape with an outer wall formed as a cylindrical tube 12. A screw blade 14 taking the shape of a helix is provided within the cylindrical tube 12 with the outer edge of the screw blade 14 being fixed to the inner wall of the cylindrical tube 12. This may be done, for example, by welding. It is beneficial to ensure that a watertight seal is formed between the outer edge of the screw blade 14 and the inner wall of the cylindrical tube 12, since this means that multiple chambers 16 can be formed, with a chamber 16 in between each 360 degree turn of the screw blade 14. A plurality of mixing devices 18 are provided on the surface of the screw blade 14 at the outer edge thereof. There are multiple mixing devices 18 for each 360 degree turn of the screw blade 14, and as shown in this example there can be eight for each 360 degree turn of the screw blade 14.

Figure 5:
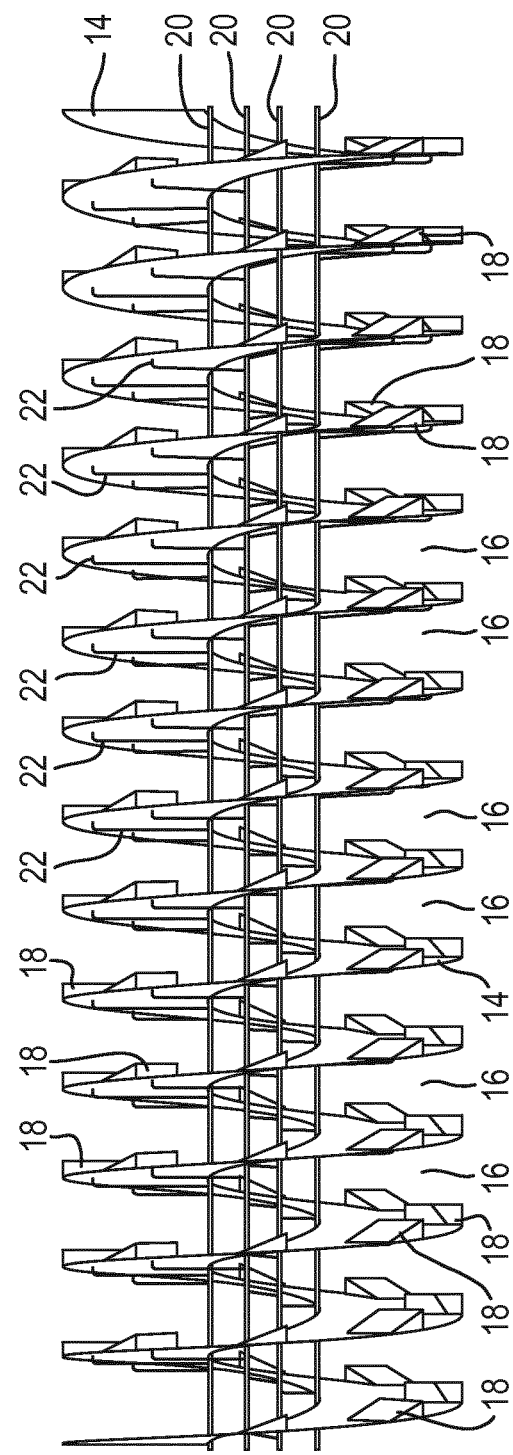
FIG. 5 shows a screw blade with mixing devices as used in the drum of FIG. 4.

The mixing devices 18 and the screw blade 14 can be seen more clearly in FIG. 5 where the cylindrical tube 12 is removed for clarity. FIG. 5 also shows pipework used to supply fluid to the mixing device 18, including central supply pipes 20 and branch pipes 22 extending to each individual mixing device 18. In this example the material within the rotating drum, which may for example be a mixture of solid and liquid elements forming a slurry or the like, would sit in each chamber 16 between adjacent turns of the screw blade 14 and extend up the screw blade toward the centre of the rotating drum by about 50% of the height of the screw blade 14, for example.

Figure 6:
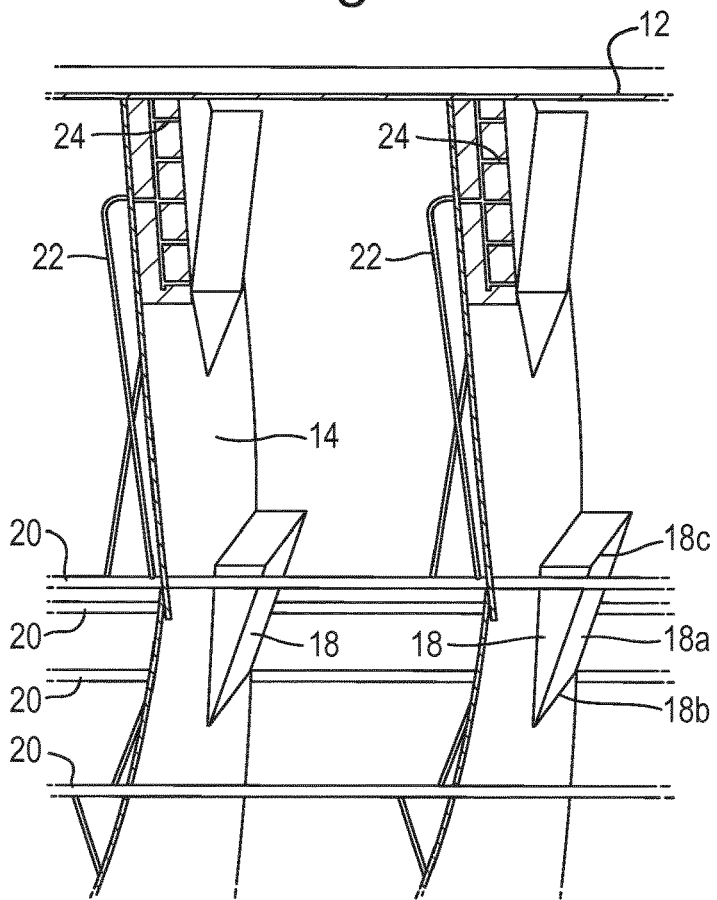
FIG. 6 is a close up view of a part of the screw blade of FIG. 5.
Figure 7:
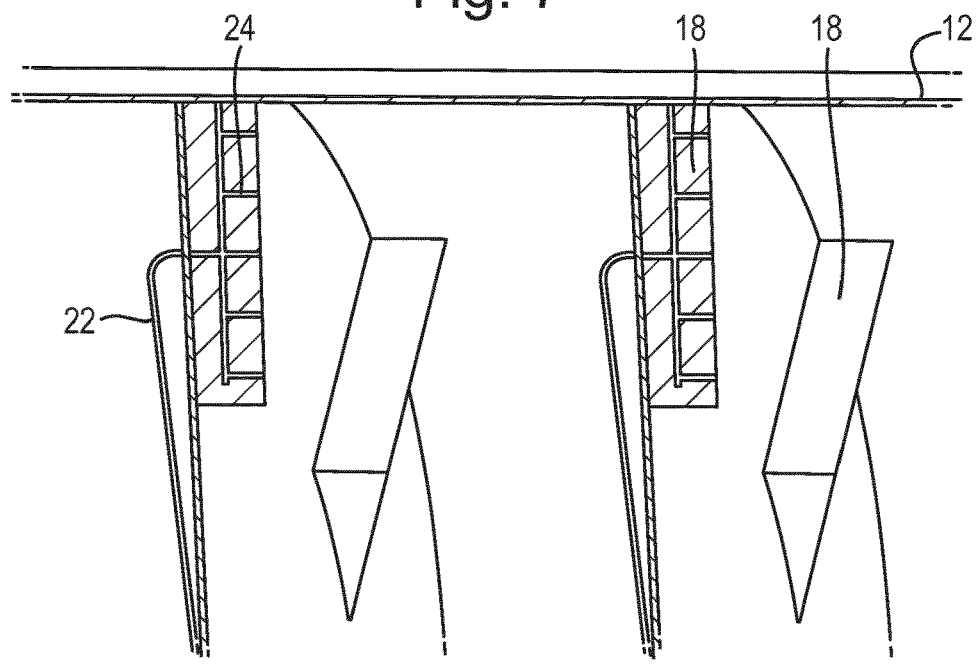
FIG. 7 is a further close up of a part of FIG. 6.

The mixing devices 18 will now be described in greater detail with reference to FIG. 6 and FIG. 7. FIG. 6 shows a part of two turns of the screw blade 14 in enlarged view with one of the mixing devices 18 at the top of the figure shown in partial section view. FIG. 7 shows a close-up of the top of FIG. 6 so that further detail can be seen. Each of the mixing devices 18 comprises a wedge shaped mixing vane and fluid inlets. The mixing vane in this example has a side profile of the shape of a right-angled triangle with one surface of the triangle being coupled to the surface of the screw blade 14, a vertical surface of the triangle extending at right angles from the surface of the screw blade 14 and a ramp surface of the triangle providing the mixing vane surface 18a. The ramp surface of the triangle extends from a leading edge 18b at the narrow point of the triangle to a trailing edge 18c at the apex of the triangle that is furthest from the screw blade 14. The trailing edge of the mixing vane is provided with fluid inlets 24 which convey fluid supplied via the pipes 20 and branch pipes 22 through the mixing device 18 and out of the inlets 24 into the rotating drum.

The processing plant of FIG. 3 and/or the rotating drum of FIGS. 4 to 7 may be used for other processes as well, and provide advantages for any process requiring constant mixing and/or relatively long reaction times. Various possible processes are set out in the examples below:

EXAMPLE

Hydrolysis Process 1

The process uses a corrugated pipe with whole sardines (anchovy) with Alcalase (Novozymes), ground through 6 mm dyes, a raw material/water ratio 50/50 (w/w), which may be mixed using the rotating drum, and a reaction temperature 60° C. Targeted % DH=17 (% DH=number of peptide bonds cleaved/total number of peptide bonds), estimated reaction time 45 minutes based on info from the enzyme manufacturer. The enzyme added is 0.1% (d·w) of raw material (w·w) excluding added water. The plant is operated with a capacity 7 MT per hour, of which 3.5 MT of fish and 3.5 MT of water. The tube length will be 863 m when a corrugated pipe is used for the hydrolysis stage. It will be appreciated that a suitably sized rotating drum with an appropriate speed of rotation might be used as an alternative apparatus for the hydrolysis stage.

Supplementary Information:

In this case no large bone particles are present, and thus the risk of clogging due to sedimentation of hard particles is low. The whole length of the tube is of similar shape and diameter throughout, although viscosity decreases down the line. A boost pump is fitted in ⅓ the length from the inlet as a safety guard towards clogging. The concentration of peptides increases with time as protein hydrolysis goes on. Peptides can act as emulgators, and a key point is to avoid the formation of emulsions along the tube.

Reaction Mixture Properties:

Density $\mu=1000$ kg/m$^3$

Viscosity $\rho=25$ cP (inlet)

Selected Properties of the Flow:

Reynolds number Re=1125

Mean velocity v=0.32 m/s

Using these parameters gives the diameter D=88 mm. For the parameter values given above, this example has a volume flow rate of 7 m$^3$/h.

EXAMPLE

Hydrolysis Process 2

This example uses a corrugated pipe with raw material (heads and backbones from salmon or chicken frames) to be hydrolysed using Protamex (Novozymes). The enzyme concentration is 0.1% (d·w) of raw material (w·w). The raw material undergoes grinding through 6 mm dyes, and is mixed in a ratio of raw material/water 50/50 (w/w) optionally via the rotating drum, before being processed at a reaction temperature of 50° C. The targeted degree of hydrolysis % DH=10 (% DH=number of peptide bonds cleaved/total number of peptide bonds), and the estimated reaction time 30 minutes based on information from the enzyme manufacturer. Again, a rotating drum with suitable dimensions and an appropriate rotation speed could be substituted for the corrugated pipe.

Supplementary Information:

In this case where large bone particles are present the optimal configuration of the hydrolysis unit is a first part (⅓) where there is less risk of sedimentation of the bone particles resulting in a clogged tube—due to relative high viscosity. As process runs then the viscosity declines increasing the risk of clogging. Therefore, in this embodiment the hydrolysis unit is constructed by means of three different tube diameters linked together. Optionally there may be a filtering system after mixing in order to remove larger bone particles.

The hydrolysis unit parameters are given below for the pipe inlet, at the mid-length and at the pipe outlet.

Reaction Mixture Properties:

Density $\mu=1000$ kg/m$^3$

Viscosity $\rho=33$ cP, 25 cP and 20 cP

Selected Properties of the Flow:

Reynolds number Re=853, 1415, 1956

Mean velocity v=0.32 m/s, 0.51 m/s and 0.62 m/s

Using these parameters gives diameters of D=88 mm start, 70 mm in mid-section and 63.2 mm the last part. The total tube length is 866 m, distributed into 192 m first part, 303 m mid part and 371 m last part. There will be a boost pump before section 2 and before section 3. The volume flow rate for this example would be 7 m$^3$/h.

EXAMPLE

Hydrolysis Process 3

In this case hydrolysate processed from salmon frames and heads by means of Alcalase (Novozymes) is further processed through a secondary hydrolysis using Flavourzyme (Novozymes) which is an exopeptidase/endopeptidase complex specially designed to optimize taste and reduce bitterness. The hydrolysate was diluted to contain 10% dry matter, of which protein is the major part (approx. 90%). The substrate contains virtually no lipids. The reaction time is 20 minutes and the reaction temperature 55° C. The enzyme concentration is 0.1% (d·w) of raw material (w·w).

Supplementary Information:

In this case the substrate is a free-flowing liquid with no particles nor lipids are present, and thus there is no risk of clogging or formation of emulsions. Viscosity is low throughout the process tube, which is of similar construction throughout.

The following exemplary calculation uses values for the parameters which may be typical of a working system:

Reaction Mixture Properties:

Density $\mu=1040$ kg/m$^3$

Viscosity $\rho=6.5$ cP

Selected Properties of the Flow:

Reynolds number Re=1811

Mean velocity v=0.09 m/s

Using these parameters gives the pipe diameter D=125 mm. The tube length is 109 m. For the parameter values given above, the volume flow rate is 4 m$^3$/h.

EXAMPLE

Rotating Drum 1

Basic Example Data:

Capacity: Approx 30 m$^3$ per hour (15 tons raw material and 15 tons of water)

Processing time: 1 hour

Density: 1000 kg/m$^3$

Drum diameter: 3.5 m

Drum diameter inner opening: 1 meter

Drum length: 11.75 m

Comments: Calculation by means of «Solidworks» show that an outer diameter of 3.5 m, length 11.75 m, inner opening 1 m and 15 cm between liquid level and top of the screw blades—exclusive of the volume of screw blades and mixing vanes—gives a total liquid volume of 30,421 litre.

The incline of the screw is linked to the rotational speed of the drum. High incline gives few "chambers" resulting in a more "batchlike" process. An example configuration (present example) with 750 mm between the vanes with a rotation of ¼ revolution/min gives a periphery speed of 0.0458 m/s.

Nozzles are integrated within each vane as fluid inlets to supply fluid to the rotating drum during mixing. The angled vane propels particles away from the surface of the screw blade, the screw blade continues to rotate and the particles are "launched" from the trailing edge of the vane, whereafter there is turbulent mixing. When the next vane meets the material in the drum the particles in the material would be close to the screw blade again (to be calculated depending on space between screw blade and vane size in each case). By having nozzles along the edge of the vane a very effective mixing is promoted, since the fluid is injected into the zone of turbulent mixing The vanes in this example could have a height of 500 mm with nozzles mounted 50, 150, 250, 350 and 450 mm from the outer wall of the drum. The maximum height of liquid in the drum will be 1.1 m, but the vane height is 500 mm rather than the full extent of the screw blade or the liquid level since particles will aggregate near the bottom of the rotating drum.

One nozzle typically delivers 10 litre per hour. Having 8 vanes with 5 nozzles each per revolution give a total of (8×15×10)=600 nozzles. Active nozzles (activated when submerged only) will constitute 38% —that is 600× 0.38=228 active nozzles a run of one hour.

If we anticipate nozzles ejecting 10 l/hour, which means that the addition of water will be 228×10=2280 l/hour. This gives a volume increase of 7.6% —or increase in liquid level of approximately 6 cm for the chambers at the outlet end of the drum compared to at the inlet end. While this may not be a problem, a steady level could be obtained either by a slight and steady increase of the pitch/angle of attack of the screw blade along the length of the drum or a slight downwards tilt of the drum.

EXAMPLE

Rotating Drum 2

A drum of 2.5 m diameter, 75 cm inner opening and 5.5 m length would have a capacity of 7.13 m³ (liquid level 10 cm below top of the screw blade, calculated without volume of the screw blade and the vanes). This could be mixed with a screw blade of similar characteristics to that shown in the Figures, but with a reduced number of vanes (for example five vanes for each turn of the screw blade) to allow for an increased mixing volume.

EXAMPLE

Outlet Arrangement for Rotating Drum 1

The first example drum discussed above has a rotational speed of ¼ rotations per minute, that is 240 seconds per revolution. The final chamber has a liquid volume of about 2000 litres. Having an even flow rate out from the drum will make it easier to handle the material from the drum during the next processing steps. In addition, it is an advantage to drain from the bottom of the chamber to avoid separating the liquid from the solid, otherwise all the solid material will be discharged at the end. An even flow rate with a mixture of solid and liquid can be provided by having small holes/openings in the final turn of the screw blade, thereby distributing the discharge flow over the entire revolution of the drum. The openings can be distributed along the entire outer diameter and/or distributed along the blade with different distances from the centre of the drum. To describe this mathematically is quite complex, but it is theoretically possible to obtain a flow out of the drum of less than 12 litre/second.

The openings can be constructed with adjustable sizes, including the possibility to block some of the openings. Having an adjustable total area for the openings allows the flow rate to be adapted for differing volumes of material and/or for differing mixtures of liquid and solid materials. The adjustable openings can be implemented by sliding plates or exchangeable plates connected to the surface of the screw blade.

Calculations based on a variant of Bernouillis equation called Toricellis law, which describes the flow from a tank, can be made to determine the flow rate, with approximations allowing for friction of the liquid/solid material and the design of the outlet, as well as assumptions regarding the effect on the flow rate of the rotation of the drum. To set an opening size that will fully empty the chamber within one revolution then the calculations can be based on emptying during three quarters of a revolution. Fine tuning of the opening time can be done via experiments and/or during first operation, for example by blocking some of the openings if the flow rate is too high.

In this case the calculation shows that it is necessary to have openings under the surface of the material in the drum with a total area of about 72 cm². To avoid that hard particles (crab shells, larger sized bones etc.) will clog the openings then they need to have a certain minimum size. In this example we use openings of 25×40 mm, so that each opening has an area of 10 cm². This means that about 7 openings are needed under the surface of the material of the drum. Assuming that the material of the drum has a level that is similar to a chord subtending an arc of 60°, and the screw blade is open for 90° of perimeter of the final turn then in total around 32 openings are needed spaced apart over the final 270° of the screw blade. Even if this calculation is very simplified, it shows that due to the low rotational speed only relatively few openings that are relatively small compared to the drum size are needed to empty the last chamber. Thus, such openings can easily be placed and designed in a way resulting in an even and controlled flow rate out of the drum.

The invention claimed is:

1. A rotating drum apparatus for the mixing and processing of materials, the rotating drum apparatus comprising:
    a rotating drum arranged with a length of the drum and an axis of rotation of the drum extending horizontally;
    an inlet at a first point on the drum for receiving materials prior to mixing and/or processing;
    a screw within the drum for mixing the materials while conveying the materials lengthwise along the drum, wherein the screw includes a helical blade extending along the length of the drum with an outer edge of the helical blade being fixed to an inner surface of the drum such that the materials can be conveyed and mixed in separated volumes between each 360 degree turn of the helical blade of the screw;
    an outlet at a second point along the drum for discharge of the materials after mixing and/or processing of the materials; and
    a plurality of mixing devices for promoting mixing of the materials in each of the separated volumes of the materials as the materials are conveyed along the screw, wherein mixing devices of the plurality of mixing devices are spaced apart along the helical blade of the screw, wherein at least one mixing device of the plurality of mixing devices is provided for each 360 degree turn of the helical blade of the screw, and wherein the mixing devices comprise fluid inlets for the addition of fluid to the mixture within each volume between 360 degree turns of the helical blade of the screw.

2. The rotating drum apparatus as claimed in claim 1, comprising multiple mixing devices for each 360 degree turn of the helical blade of the screw.

3. The rotating drum apparatus as claimed claim 1, wherein the plurality of mixing devices comprises mixing vanes spaced apart along the screw with multiple vanes for each 360 degree turn of the helical blade of the screw, the mixing vanes being arranged to promote mixing of the materials in the rotating drum.

4. The rotating drum apparatus as claimed in claim 3, comprising at least one of the following features (a) or (b): (a) the mixing vanes comprise an element mounted to the helical blade of the screw with a ramp surface having a greater angle of attack than a surface of the helical blade of the screw, or (b) the mixing vanes are mounted at an outer part of the surface of the helical blade of the screw adjacent to the inner surface of the drum and extend from the inner surface of the drum along the surface of the helical blade of the screw toward the axis of rotation of the drum.

5. The rotating drum apparatus as claimed in claim 3, wherein a height of the mixing vanes is at least 20% of a height of the helical blade of the screw.

6. The rotating drum apparatus as claimed in claim 1, wherein the mixing devices comprise fluid inlets opening into the drum at a trailing edge of the mixing vanes.

7. The rotating drum apparatus as claimed in claim 1, wherein the fluids introduced by the fluid inlets are at an elevated or lowered temperature compared to the temperature of the materials within the drum.

8. The rotating drum apparatus as claimed in claim 1, comprising fluid flow control devices for controlling the rate of flow of fluid through the fluid inlets.

9. The rotating drum apparatus as claimed in claim 8, comprising a controller arranged to permit flow through fluid inlets that are immersed within the material that is being mixed, and to prevent flow when the fluid inlets are not within the material that is being mixed.

10. The rotating drum apparatus as claimed in claim 9, wherein the controller comprises switching devices located adjacent to an expected level of the materials within the drum, such that individual fluid inlets are activated and deactivated in accordance with the state of the switching devices as the switching devices cause the materials to enter into or exit from the material at a base of the drum.

11. The rotating drum apparatus as claimed in claim 1, wherein the helical blade of the screw has a change in pitch between the inlet and the outlet.

12. The rotating drum apparatus as claimed in claim 1, further comprising one of the following features (i) or (ii): (i) the separated volumes formed between adjacent turns of the helical blade of the screw are open to a hole at a center of the drum, or (ii) the separated volumes formed between adjacent turns of the helical blade of the screw are closed by a cylindrical body along the center of the drum and that is fixed to an inner edge of the helical blade of the screw.

13. The rotating drum apparatus as claimed in claim 1, wherein the drum and/or the helical blade of the screw are provided with outlet features during a final turn of the helical blade of the screw in order to provide a more even flow rate from the outlet of the drum, wherein the outlet features include holes in the wall of the drum and/or holes in the surface of the helical blade of the screw during the final turn of the helical blade of the screw.

14. The rotating drum apparatus as claimed in claim 13, wherein holes are provided with openings through the final turn of the helical blade of the screw in order to provide for fluid communication between (i) a separated volume formed between the final turn and a penultimate turn of the helical blade of the screw and (ii) an outlet end of the rotating drum.

15. The rotating drum apparatus as claimed in claim 13, wherein a total area of holes is sufficient to allow for all of the materials within the separated volume formed between the final turn and a penultimate turn of the screw to flow out toward the outlet end of the drum through the final turn of the helical blade of the screw during one turn of the drum.

16. The rotating drum apparatus as claimed in claim 13, further comprising at least one of the following features (a) to (c): (a) a total area of the holes beneath the expected level of materials in the drum is in the range of 40-200 cm$^2$; (b) a total area of all of the holes is 180-850 cm$^2$ with the holes spaced about a circumference of the final turn of the helical blade of the screw; or (c) the holes are of adjustable size.

17. The rotating drum apparatus as claimed in claim 1, further comprising at least one of the following features (a) or (b): (a) a diameter of the drum is at least 2 m, or (b) the length of the drum between the inlet and the outlet is at least 3 m.

18. An enzymatic processing plant configured for hydrolysis of protein, triglycerides, cellulose, or chitin, the processing plant comprising a rotating drum apparatus as claimed in claim 1.

19. An enzymatic processing plant configured for enzymatic processing of organic molecules, the enzymatic processing plant comprising: at least one enzymatic processing area that comprises a rotating drum apparatus as claimed in claim 1 configured to mix a reaction mixture flowing through the enzymatic processing area, wherein the enzymatic processing plant and the enzymatic processing area are arranged such that the reaction mixture is subjected to turbulence and/or mixing within the enzymatic processing area of the rotating drum for a reaction time of at least 15 minutes.

20. A kit of parts for making an enzymatic processing plant for enzymatic processing of organic compounds in a reaction mixture, the kit of parts comprising: a pump for pumping the reaction mixture through the enzymatic processing plant; a first enzymatic processing area for performing a first stage of enzymatic processing; and a separator system comprising a decanter for separating a flow of water soluble components, oil-soluble components and solid components; and the kit of parts further comprising one or more of: a filter; a second enzymatic processing area; a third enzymatic processing area; a flow division stage; a flow combining stage; an injection point; a mixing chamber; a heat inactivation stage; a polisher; and a drier;

wherein at least one enzymatic processing area of the first, second, and third enzymatic processing areas comprises a rotating drum apparatus as claimed in claim 1.

21. A method of mixing and/or processing materials, the method comprising:

feeding materials requiring mixing and/or processing into a rotating drum apparatus as claimed in claim 1 via an inlet at a first point on the drum;

rotating the drum and thereby mixing the materials while conveying the materials lengthwise along the drum using a screw within the drum, wherein the screw includes a helical blade extending along the length of the drum with an outer edge of the helical blade being fixed to an inner surface of the drum such that the materials can be conveyed and mixed in separated volumes between each 360 degree turn of the helical blade of the screw; and discharging materials after mixing and/or processing from an outlet at a second point along the drum.

22. A method of manufacturing a modular enzymatic processing plant for enzymatic processing of a reaction mixture, the method comprising determining a required enzymatic processing process and manufacturing a suitable enzymatic processing plant from a kit of modular parts by providing:

a pump for pumping the reaction mixture through the enzymatic processing plant;

a first enzymatic processing area for performing a first stage of enzymatic processing, the first enzymatic processing area including a rotating drum apparatus as claimed in claim 1; and a separator system comprising a decanter for separating a flow of water soluble components, oil-soluble components and solid components.

\* \* \* \* \*